(12) United States Patent
Yu et al.

(10) Patent No.: US 12,290,505 B2
(45) Date of Patent: *May 6, 2025

(54) TISSUE FACTOR-TARGETED ANTIBODY-DRUG CONJUGATE

(71) Applicants: FUDAN UNIVERSITY, Shanghai (CN); SHANGHAI INSTITUTE OF MATERIA MEDICA, CHINESE ACADEMY OF SCIENCES, Shanghai (CN); SHANGHAI MIRACOGEN INC., Shanghai (CN)

(72) Inventors: Ke Yu, Shanghai (CN); Jingkang Shen, Shanghai (CN); Tao Meng, Shanghai (CN); Lanping Ma, Shanghai (CN); Xuesai Zhang, Shanghai (CN); Qingrou Li, Shanghai (CN); Qing Lin, Shanghai (CN)

(73) Assignees: FUDAN UNIVERSITY, Shanghai (CN); SHANGHAI INSTITUTE OF MATERIA MEDICA, CHINESE ACADEMY OF SCIENCES, Shanghai (CN); SHANGHAI MIRACOGEN INC., Shanghai (CN)

( * ) Notice: Subject to any disclaimer, the term of this patent is extended or adjusted under 35 U.S.C. 154(b) by 127 days.

This patent is subject to a terminal disclaimer.

(21) Appl. No.: 18/050,240

(22) Filed: Oct. 27, 2022

(65) Prior Publication Data

US 2023/0138930 A1 May 4, 2023

Related U.S. Application Data

(63) Continuation of application No. 16/326,886, filed as application No. PCT/CN2017/087779 on Jun. 9, 2017, now Pat. No. 11,534,495.

(30) Foreign Application Priority Data

Aug. 22, 2016 (CN) .......................... 201610704559.1
Mar. 3, 2017 (CN) .......................... 201710125244.6

(51) Int. Cl.
| | | |
|---|---|---|
| *A61K 39/395* | (2006.01) | |
| *A61K 31/40* | (2006.01) | |
| *A61K 31/4025* | (2006.01) | |
| *A61K 31/5365* | (2006.01) | |
| *A61K 31/537* | (2006.01) | |
| *A61K 47/54* | (2017.01) | |
| *A61K 47/68* | (2017.01) | |
| *A61P 35/00* | (2006.01) | |
| *C07K 16/36* | (2006.01) | |

(52) U.S. Cl.
CPC .......... *A61K 31/40* (2013.01); *A61K 31/4025* (2013.01); *A61K 31/5365* (2013.01); *A61K 31/537* (2013.01); *A61K 47/542* (2017.08); *A61K 47/545* (2017.08); *A61K 47/68* (2017.08); *A61K 47/68031* (2023.08); *A61K 47/68033* (2023.08); *A61K 47/6843* (2017.08); *A61P 35/00* (2018.01); *C07K 16/36* (2013.01); *C07K 2317/24* (2013.01); *C07K 2317/565* (2013.01); *C07K 2317/90* (2013.01)

(58) Field of Classification Search
None
See application file for complete search history.

(56) References Cited

U.S. PATENT DOCUMENTS

| | | | |
|---|---|---|---|
| 6,274,142 B1 | 8/2001 | O'Brien et al. | |
| 7,579,000 B2 | 8/2009 | Light et al. | |
| 7,605,235 B2 | 10/2009 | Anderson et al. | |
| 7,749,498 B2 | 7/2010 | Jiao et al. | |
| 7,968,094 B2 | 6/2011 | Jiao et al. | |
| 10,676,537 B2 * | 6/2020 | Yu | .............. A61P 7/02 |
| 11,534,495 B2 * | 12/2022 | Yu | ............ A61K 31/40 |
| 2014/0079628 A1 | 3/2014 | Anderson et al. | |
| 2014/0234304 A1 | 8/2014 | Almagro et al. | |
| 2016/0053020 A1 | 2/2016 | Verploegen et al. | |

FOREIGN PATENT DOCUMENTS

| | | | | |
|---|---|---|---|---|
| CN | 1575302 A | 2/2005 | | |
| CN | 102317319 A | 1/2012 | | |
| CN | 103119065 A | 5/2013 | | |
| CN | 103342752 A | 10/2013 | | |
| CN | 104387474 A | 3/2015 | | |
| CN | 106467574 A | 3/2017 | | |
| CN | 110575547 A | 12/2019 | | |
| EP | 3 502 141 A1 | 6/2019 | | |
| WO | WO-9405328 A1 * | 3/1994 | ........... C07K 14/745 | |
| WO | 03/029295 A1 | 4/2003 | | |
| WO | 2005/025623 A2 | 3/2005 | | |
| WO | WO-2007056352 A2 * | 5/2007 | ............. C07K 16/36 | |
| WO | 2008/137382 A1 | 11/2008 | | |

(Continued)

OTHER PUBLICATIONS

Foote et al., J Mol Biol. Mar. 20, 1992;224(2):487-99. doi: 10.1016/0022-2836(92)91010-m. PMID: 1560463.*
Dondelinger et al., Front Immunol. Oct. 16, 2018:9:2278. doi: 10.3389/fimmu.2018.02278. eCollection 2018. PMID: 30386328 PMCID: PMC6198058.*
Lambert et al., Annu Rev Med. Jan. 29, 2018:69:191-207. doi: 10.1146/annurev-med-061516-121357. PMID: 29414262.*
Supplementary European Search Report corresponding to European Application No. EP 17 84 2543.5, 9 pages, dated Mar. 11, 2020.
Office Action, Chinese Application No. 201610705557.4, dated Mar. 28, 2019.

(Continued)

*Primary Examiner* — Michael Szperka
(74) *Attorney, Agent, or Firm* — Seed IP Law Group LLP

(57) ABSTRACT

A tissue factor (TF)-targeted antibody-drug conjugate (ADC) and a method for preparing the ADC. The ADC is capable of binding to TF antigen with high specificity, and has high affinity, low immunogenicity, high cytotoxicity, and significant anti-tumor activity.

13 Claims, 12 Drawing Sheets

Specification includes a Sequence Listing.

(56) References Cited

FOREIGN PATENT DOCUMENTS

| WO | WO-2011157741 A2 | * | 12/2011 | ........... A61K 39/395 |
|---|---|---|---|---|
| WO | 2015/075201 A1 | | 5/2015 | |
| WO | 2015/115656 A1 | | 8/2015 | |
| WO | 2015/157595 A1 | | 10/2015 | |
| WO | 2017/028823 A1 | | 2/2017 | |

OTHER PUBLICATIONS

International Search Report for Application No. PCT/CN2017/074163, dated May 25, 2017 (English Translation).

Qu et al., "Molecular Mechanism of Tissue Factor in Cardiovascular Disease and Significance Thereof," *Chinese Circulation Journal*, p. 480, non-official translation, Dec. 31, 2007.

Hembrough et al., "Tissue Factor/Factor VIIa Inhibitors Block Angiogenesis and Tumor Growth Through a Nonhemostatic Mechanism," *Cancer Research* 63:2997-3000 (Jun. 1, 2003).

Hu et al., "Opposite regulation by PI3K/Akt and MAPK/ERK pathways of tissue factor expression, cell-associated procoagulant activity and invasiveness in MDA-MB-231 cells," *Journal of Hematology & Oncology* 5:16, 10 pages (2012).

Lambert et al., "Antibody-Drug Conjugates (ADCs) for Personalized Treatment of Solid Tumors: A Review," *Adv Ther* 34:1015-1035 (2017).

Theunissen et al., "Treating Tissue Factor-Positive Cancers with Antibody-Drug Conjugates That Do Not Affect Blood Clotting," *Mol Cancer Ther* 17(11):2412-2426 (Nov. 2018).

Unruh et al., "Antibody-based targeting of alternatively spliced tissue factor: a new approach to impede the primary growth and spread of pancreatic ductal adenocarcinoma," *Oncotarget* 7(18):25264-25275 (Mar. 7, 2016).

Zhang et al., "Pathological expression of tissue factor confers promising antitumor response to a novel therapeutic antibody SC1 in triple negative breast cancer and pancreatic adenocarcinoma," *Oncotarget* 8(35):59086-59102 (2017).

* cited by examiner

| IC$_{50}$ (TF-mAb-DM1) | |
|---|---|
| Cell line | Concentration (nM) |
| MDA453 | >100 |
| A549 | >100 |
| MCF7 | 100 |
| T47D | >100 |
| U87MG | 17.203±0.928 |
| H1975 | 25.395±4.482 |
| MDA231 | 0.098±0.025 |
| HCC1806 | 0.022±0.006 |
| BxPC3 | 0.038±0.005 |
| Hs578T | 0.074±0.009 |

| IC$_{50}$ (TF-mAb-MMAE) | |
|---|---|
| Cell line | Concentration (nM) |
| MDA453 | >100 |
| MCF7 | >100 |
| T47D | >100 |
| A549 | >100 |
| H1975 | 0.549±0.065 |
| U87MG | 32.491±5.362 |
| MDA231 | 0.112±0.014 |
| HCC1806 | 0.088±0.01 |
| BxPC3 | 0.049±0.003 |

| IC$_{50}$ (TF-mAb-H39-MMAE) ||
|---|---|
| Cell line | Concentration (nM) |
| MDA453 | >100 |
| T47D | >100 |
| PANC-1 | >100 |
| HCC38 | 0.180±0.028 |
| MDA231 | 0.024±0.006 |
| HCC1937 | 0.053±0.019 |
| HCC1806 | 0.046±0.01 |
| BxPC3 | 0.023±0.001 |

SEQUENCE LISTING

```
Sequence total quantity: 17
SEQ ID NO: 1            moltype = AA  length = 5
FEATURE                 Location/Qualifiers
source                  1..5
                        mol_type = protein
                        organism = Mus musculus
SEQUENCE: 1
SYWMN                                                                  5

SEQ ID NO: 2            moltype = AA  length = 17
FEATURE                 Location/Qualifiers
source                  1..17
                        mol_type = protein
                        organism = Mus musculus
SEQUENCE: 2
MIYPADSETR LNQKFKD                                                    17

SEQ ID NO: 3            moltype = AA  length = 8
FEATURE                 Location/Qualifiers
source                  1..8
                        mol_type = protein
                        organism = Mus musculus
SEQUENCE: 3
EDYGSSDY                                                               8

SEQ ID NO: 4            moltype = AA  length = 10
FEATURE                 Location/Qualifiers
source                  1..10
                        mol_type = protein
                        organism = Mus musculus
SEQUENCE: 4
SASSSVSYMN                                                            10

SEQ ID NO: 5            moltype = AA  length = 7
FEATURE                 Location/Qualifiers
source                  1..7
                        mol_type = protein
                        organism = Mus musculus
```

```
SEQUENCE: 5
GISNLAS                                                                   7

SEQ ID NO: 6             moltype = AA  length = 9
FEATURE                  Location/Qualifiers
source                   1..9
                         mol_type = protein
                         organism = Mus musculus
SEQUENCE: 6
QQKSSFPWT                                                                 9

SEQ ID NO: 7             moltype = AA  length = 117
FEATURE                  Location/Qualifiers
source                   1..117
                         mol_type = protein
                         organism = Mus musculus
SEQUENCE: 7
QVQLQQPGAE LVRPGASVKL SCKASGYSFI SYWMNWVKQR PGQGLEWIGM IYPADSETRL          60
NQKFKDKATL TVDKSSSTAY MQLSSPTSED SAVYYCARED YGSSDYWGQG TTLTVSS            117

SEQ ID NO: 8             moltype = AA  length = 106
FEATURE                  Location/Qualifiers
source                   1..106
                         mol_type = protein
                         organism = Mus musculus
SEQUENCE: 8
EILLTQSPAI IAASPGEKVT ITCSASSSVS YMNWYLQKPG SSPKIWIYGI SNLASGVPAR          60
FSGSGSGTSF SFTINSMETE DVATYYCQQK SSFPWTFGGG TKLEIK                       106

SEQ ID NO: 9             moltype = AA  length = 117
FEATURE                  Location/Qualifiers
REGION                   1..117
                         note = VH
source                   1..117
                         mol_type = protein
                         organism = synthetic construct
SEQUENCE: 9
EVQLVQSGAE VKKPGESLKI SCKGSGYSFT SYWMNWVRQM PGKGLEWMGM IYPADSETRL          60
NQKFKDQATL SVDKSISTAY LQWSSLKASD TAMYYCARED YGSSDYWGQG TTVTVSS            117

SEQ ID NO: 10            moltype = AA  length = 117
FEATURE                  Location/Qualifiers
REGION                   1..117
                         note = VH
source                   1..117
                         mol_type = protein
                         organism = synthetic construct
SEQUENCE: 10
EVQLVQSGAE VKKPGESLKI SCKGSGYSFT SYWMNWVRQM PGKGLEWMGM IYPADSETRL          60
NQKFKDKATL SVDKSISTAY LQWSSLKASD TAMYYCARED YGSSDYWGQG TTVTVSS            117

SEQ ID NO: 11            moltype = AA  length = 117
FEATURE                  Location/Qualifiers
REGION                   1..117
                         note = VH
source                   1..117
                         mol_type = protein
                         organism = synthetic construct
SEQUENCE: 11
EVQLVQSGAE VKKPGESLKI SCKGSGYSFT SYWMNWVKQM PGKGLEWMGM IYPADSETRL          60
NQKFKDKATL SVDKSISTAY LQWSSLKASD TAMYYCARED YGSSDYWGQG TTVTVSS            117

SEQ ID NO: 12            moltype = AA  length = 117
FEATURE                  Location/Qualifiers
REGION                   1..117
                         note = VH
source                   1..117
                         mol_type = protein
                         organism = synthetic construct
SEQUENCE: 12
QVQLVQSGAE VKKPGASVKV SCKASGYSFI SYWMNWVRQA PGQGLEWIGM IYPADSETRL          60
NQKFKDRATL TVDKSTSTAY MELSSLRSED TAVYYCARED YGSSDYWGQG TTVTVSS            117

SEQ ID NO: 13            moltype = AA  length = 117
FEATURE                  Location/Qualifiers
REGION                   1..117
                         note = VH
source                   1..117
                         mol_type = protein
```

```
                          organism = synthetic construct
SEQUENCE: 13
QVQLVQSGSE LKKPGASVKV SCKASGYSFI SYWMNWVRQA PGQGLEWIGM IYPADSETRL    60
NQKFKDRAVL SVDKSVSTAY LQICSLKAED TAVYYCARED YGSSDYWGQG TTVTVSS      117

SEQ ID NO: 14             moltype = AA  length = 106
FEATURE                   Location/Qualifiers
REGION                    1..106
                          note = VL
source                    1..106
                          mol_type = protein
                          organism = synthetic construct
SEQUENCE: 14
EIVLTQSPAT LSLSPGERAT LSCSASSSVS YMNWYQQKPG QAPRIWIYGI SNLASGIPAR    60
FSGSGSGTDF TLTISSLEPE DFAVYYCQQK SSFPWTFGGG TKVEIK                  106

SEQ ID NO: 15             moltype = AA  length = 106
FEATURE                   Location/Qualifiers
REGION                    1..106
                          note = VL
source                    1..106
                          mol_type = protein
                          organism = synthetic construct
SEQUENCE: 15
EIVLTQSPAT LSLSPGERAT LSCSASSSVS YMNWYQQKPG QSPRIWIYGI SNLASGVPAR    60
FSGSGSGTDF TLTISSLEPE DFAVYYCQQK SSFPWTFGGG TKVEIK                  106

SEQ ID NO: 16             moltype = AA  length = 106
FEATURE                   Location/Qualifiers
REGION                    1..106
                          note = VL
source                    1..106
                          mol_type = protein
                          organism = synthetic construct
SEQUENCE: 16
DIQLTQSPSS LSASVGDRVT ITCSASSSVS YMNWYQQKPG KSPKIWIYGI SNLASGVPSR    60
FSGSGSGTDF TLTISSLQPE DFATYYCQQK SSFPWTFGGG TKVEIK                  106

SEQ ID NO: 17             moltype = AA  length = 106
FEATURE                   Location/Qualifiers
REGION                    1..106
                          note = VL
source                    1..106
                          mol_type = protein
                          organism = synthetic construct
SEQUENCE: 17
EIVLTQSPDF QSVTPKEKVT ITCSASSSVS YMNWYQQKPD QSPKIWIYGI SNLASGVPSR    60
FSGSGSGTDF TLTINSLEAE DAATYYCQQK SSFPWTFGGG TKVEIK                  106
```

TISSUE FACTOR-TARGETED ANTIBODY-DRUG CONJUGATE

CROSS REFERENCE TO RELATED APPLICATIONS

The present application is a continuation of application of U.S. application Ser. No. 16/326,886 filed Feb. 20, 2019, which is a national stage of International Application No. PCT/CN2017/087779, filed on Jun. 9, 2017, which claims priority of Chinese Patent Application No. CN201610704559.1 filed on Aug. 22, 2016 and Chinese Patent Application No. CN201710125244.6 filed on Mar. 3, 2017. U.S. application Ser. No. 16/326,886 is incorporated herein by reference in their entireties.

REFERENCE TO ELECTRONIC SEQUENCING LISTING

The contents of the electronic sequence listing (850231_403C1_SEQUENCE_LISTING.xml; Size: 20,073 bytes; and Date of Creation: Oct. 26, 2022) is herein incorporated by reference in its entirety.

TECHNICAL FIELD

The present invention relates to the medical field, particularly relates to an antibody targeted to tissue factor and an antibody-drug conjugate thereof, and preparation method and use thereof.

BACKGROUND ART

Tissue factor (TF) is a 47 kDa transmembrane glycoprotein. Under normal physiological conditions, TF expression is mainly sequestered in the layer of subendothelial cells; once the blood vessels are damaged in an organism, TF will be exposed to the blood stream, and initiate extrinsic coagulation by binding to and activating factor VII.

It has been found in studies that TF is abnormally activated and expressed in many tumor tissues, and plays an important role in the development and progression of tumors. Especially in advanced stage of cancer, most patients are accompanied by spontaneous thrombosis, such as Deep-vein thrombosis (DVT), Disseminated intravascular coagulation (DIC) and Pulmonary embolism (PE) (Thrombosis research, 2013, 131: S59-S62; Journal of Thrombosis and Haemostasis, 2011, 9(s1): 306-315). The abnormal expression of TF in tumor cells is the main cause responsible for these symptoms. Analysis on clinical samples of many tumors shows that the expression level of TF directly affects the deterioration indexes such as metastasis of tumor and occurrence of thrombosis in patients, for example, the percentage of abnormal TF expression was 85.8% in breast cancer, 88.5% in pancreatic cancer, 83.6% in lung cancer, and 91.3% in esophageal cancer, etc. (Blood, 2012, 119: 924-932).

It has been shown in studies that firstly, a TF-FVIIa complex formed by TF and FVII can directly bind to and induce the activation of a transmembrane G protein-coupled receptor, i.e. protease-activated receptor 2 (PAR2). PAR2 is an important signal pathway that regulates inflammatory response. Although there are few studies on PAR2 in the field of tumors, it is conceivable that TF can affect a series of tumor function signals in cells by virtue of PAR2. For example, TF-FVIIa-PAR2 promotes neovascularization, and provides adequate nutrients, energy and a suitable microenvironment for tumor growth by MAPK/ERK phosphorylation and inducing the gene expression of key growth factors, immunoregulators, and chemokines (e.g. VEGF, CSF1/2, IL8, CXCL1, etc.). Secondly, TF can also enhance the migration and adhesion of tumor cells by interaction with Rac1 and β1 family-related integrin, so as to enhance the hematogenous metastasis ability of tumor cells in general. Furthermore, TF-initiated coagulation is also an important cause of tumor thrombosis, and results in deterioration of a plurality of tumors. Meanwhile, TF-induced hypercoagulative state also directly helps tumor cells to evade the immune system in an organism and enhances the interaction between tumor cells and endothelial cells, resulting in an increase in the hematogenous metastasis ability. This is also an important reason why it is difficult to treat cancer.

By utilizing the characteristic that a monoclonal antibody specifically recognizes a specific antigen on the surface of tumor cells, an antibody-drug conjugate (ADC) can accurately deliver an anti-tumor drug (such as a small-molecule chemotherapeutic drug) to tumor target cells and release the drug there, so as to achieve the purpose of accurately killing tumors. ADCs are also regarded as the most potential anti-tumor drugs due to their suitable molecular weights, high stability, strong targeting property, and low toxic side effects. However, with respect to successful development of ADCs, there are also many problems that have to be taken into account and have to be solved, for example, an antibody has to specifically recognize a lesion site, has a low immunosensitization, and can be efficiently and rapidly internalized by a cell; an antibody-drug linker has to be highly stable in blood and can be specifically activated and efficiently release the small-molecule drug in the targeted cell; the conjugated small-molecule drug has a strong ability of killing cells, and so on.

It can be concluded that TF plays an important role in the development and progress of tumor, and antibody-drug conjugates have their unique characteristics and advantages, however, there still lack antibody-drug conjugates highly specific for human TF.

CONTENTS OF INVENTION

The objective of the present invention is to provide an antibody-drug conjugate, which specifically targets to human TF, has an activity of inhibiting tumor growth and metastasis, and the like.

In the first aspect, the present invention provides an antibody-drug conjugate comprising:
(a) an antibody moiety; and
(b) a conjugation moiety conjugated to the antibody moiety, wherein the conjugation moiety is selected from the group consisting of: a detectable marker, a drug, a toxin, a cytokine, a radionuclide, an enzyme, or a combination thereof;
wherein, the heavy chain variable region of the antibody comprises the following three complementary determining regions (CDRs):
CDR1 as set forth in SEQ ID NO: 1,
CDR2 as set forth in SEQ ID NO: 2, and
CDR3 as set forth in SEQ ID NO: 3;
wherein any amino acid sequence of said amino acid sequences of the heavy chain variable region further includes a derivative sequence that is optionally resulted from the addition, deletion, modification and/or substitution of at least one amino acid, and can retain a TF-binding activity;

the light chain variable region of the antibody comprises the following three complementary determining regions (CDRs):
CDR1' as set forth in SEQ ID NO: 4,
CDR2' as set forth in SEQ ID NO: 5, and
CDR3' as set forth in SEQ ID NO: 6;
a derivative sequence of any amino acid sequence of said amino acid sequences that is resulted from the addition, deletion, modification and/or substitution of at least one amino acid, and that has a TF-binding affinity.

In another preferred example, the antibody includes an intact antibody or an active fragment thereof.

In another preferred example, the active fragment retains its binding activity for tissue factor.

In another preferred example, an antibody-drug conjugate (ADC) has a formula as follows:

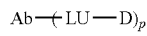

wherein:
Ab is an anti-TF antibody,
LU is a linker;
D is a drug;
and the subscript p is a value selected from 1-10, preferably from 1-8.

In another preferred example, LU is selected from the group consisting of: 6-maleimidocaproyl-valine-citrulline-p-aminobenzyloxycarbonyl (MC-val-cit-PAB), 6-maleimidocaproyl-alanine-phenylalanine-p-aminobenzyloxycarbonyl (MC-ala-phe-PAB), maleimidopropionyl-valine-citrulline-p-aminobenzyloxycarbonyl (MP-val-cit-PAB), maleimidopropionyl-alanine-phenylalanine-p-aminobenzyloxycarbonyl (MP-ala-phe-PAB), N-succinimidyl 4-(2-pyridylthio)pentanoate (SPP), N-succinimidyl 4-(N-maleimidomethyl)cyclohexane-1-carboxylate (SMCC), 4-(2-pyridyldithio)butanoic acid N-hydrosuccinimide ester (SPDB) or N-succinimidyl (4-iodo-acetyl)aminobenzoate (SIAB).

In another preferred example, LU is SMCC, SPP, SPDB or 6-maleimidocaproyl-valine-citrulline-p-aminobenzyloxycarbonyl (MC-val-cit-PAB).

In another preferred example, D is selected from the group consisting of: Maytansine derivatives (DM1, DM4), auristatin and dolastatin.

In another preferred example, the D is selected from the group consisting of: Monomethyl auristatin E (MMAE), Monomethyllauristatin F (MMAF), Monomethyl Dolastatin 10 (MMAD) derivatives or combinations thereof.

D1  DM1

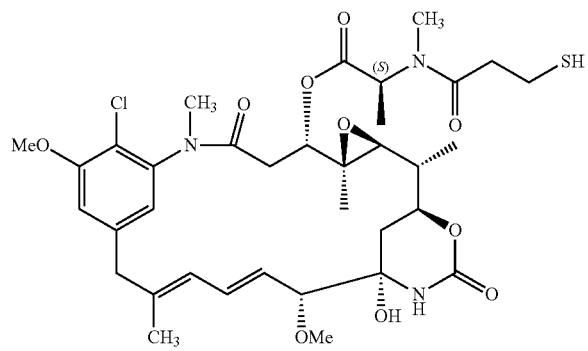

D2  DM4

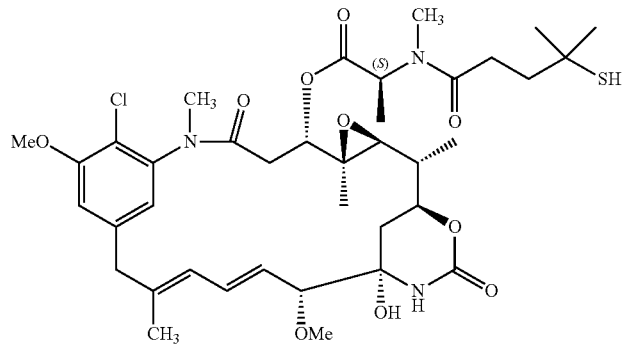

D3  Monomethyl Auristatin E (MMAE)

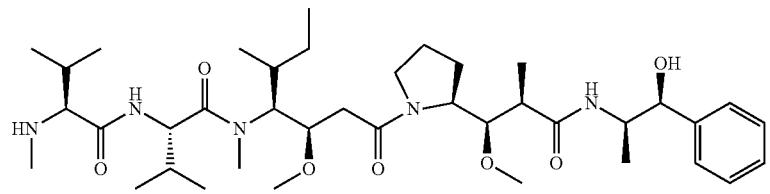 [SMILES: CCC(C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

-continued

D4  Monomethyl Auristatin F
    (MMAF)

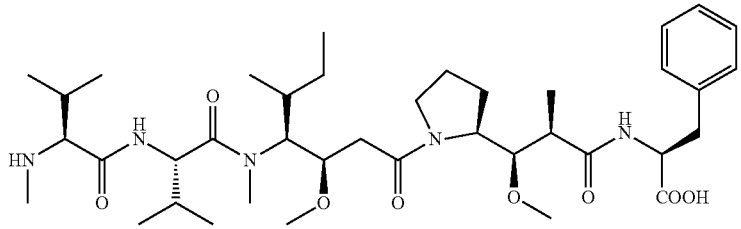 [SMILES: CCC(C)[C@@H]([C@@H](CC(=O)N1CCC[C@H]1[C@H](OC)[C@@H](C)C(=O)N[C@@H](Cc1ccccc1)C(=O)O)OC)N(C)C(=O)[C@@H](NC(=O)[C@@H](NC)C(C)C)C(C)C]

D5  Monomethyl Dolastatin 10
    (MMAD)

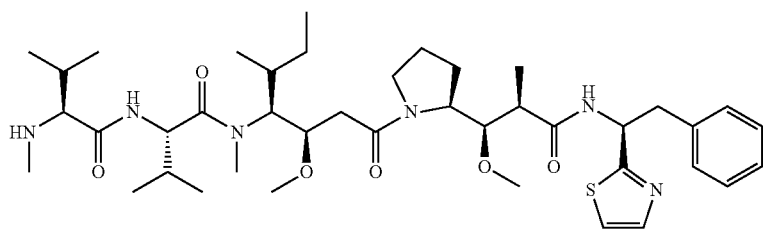 [SMILES: CCC(C)[C@@H]([C@@H](CC(=O)N1CCC[C@H]1[C@H](OC)[C@@H](C)C(=O)N[C@@H](Cc1ccccc1)c1nccs1)OC)N(C)C(=O)[C@@H](NC(=O)[C@@H](NC)C(C)C)C(C)C]

In another preferred example, the amino acid residue linked to D is originally present in the antibody (parent antibody) or is introduced exogenously.

In another preferred example, the amino acid residue linked to D is cysteine.

In another preferred example, the cysteine refers to one or more free cysteines introduced into the parent antibody at one or more positions of the light chain according to the Kabat numbering rule and/or at one or more positions of the heavy chain according to the Kabat numbering rule and at one or more positions of the heavy chain according to the EU numbering rule.

In another preferred example, the amino acid residue linked to D is lysine.

In another preferred example, the fragment is selected from: Fab, F(ab')2, Fv or scFv fragment.

In another preferred example, the antibody is a monoclonal antibody.

In another preferred example, the antibody includes: a double-chain antibody, a single-chain antibody.

In another preferred example, the antibody is recombinant.

In another preferred example, the antibody is generated in a bacterium (e.g. E. coli).

In another preferred example, the antibody is generated in an eukaryotic cell (e.g. CHO cell).

In another preferred example, the antibody is selected from: an animal-derived antibody, a chimeric antibody, a humanized antibody, or a combination thereof; more particularly, the antibody is a humanized antibody.

In another preferred example, the antibody has an $EC_{50}$ of 0.005-0.10 nM, more preferably 0.01-0.03 nM or 0.01-0.02 nM, for the affinity for human TF protein.

In another preferred example, the antibody does not bind to wild-type murine TF protein.

In another preferred example, the antibody has one or more characteristics selected from the group consisting of:
(a) inhibiting migration or metastasis of tumor cells; and
(b) inhibiting tumor growth;

In another preferred example, the sequence of the heavy chain variable region of the antibody is selected from the group consisting of: SEQ ID NO: 7, 9, 10, 11, 12, or 13; and/or the sequence of the light chain variable region of the antibody is selected from the group consisting of: SEQ ID NO: 8, 14, 15, 16, or 17.

In another preferred example, the antibody is selected from the group consisting of: TF-mAb-SC1, TF-mAb-Ch, TF-mAb-H29, TF-mAb-H30, TF-mAb-H31, TF-mAb-H32, TF-mAb-H33, TF-mAb-H34, TF-mAb-H35, TF-mAb-H36, TF-mAb-H37, TF-mAb-H38, TF-mAb-H39, TF-mAb-H40, TF-mAb-H41, TF-mAb-H42, TF-mAb-H43, TF-mAb-H44, TF-mAb-H45, TF-mAb-H46, TF-mAb-H47, and TF-mAb-H48.

In the second aspect, the present invention provides use of the antibody-drug conjugate according to the first aspect of the present invention, for (a) manufacture of a diagnostic agent; and/or (b) manufacture of a medicament for preventing and/or treating a TF-related disease.

In another preferred example, the TF-related disease is selected from: tumorigenesis, tumor growth and/or metastasis, a thrombosis-related diseases, inflammation, a metabolism-related disease, or a combination thereof.

In another preferred example, the tumor is a tumor with high TF expression.

In another preferred example, the expression "high TF expression" means that when the TF transcript and/or protein level L1 in a tumor tissue is compared with the transcript and/or protein level L0 in a normal tissue, $L1/L0 \geq 2$, preferably $\geq 3$.

In another preferred example, the tumor is selected from the group consisting of: triple negative breast cancer, pancreatic cancer, lung cancer and malignant glioma.

In the third aspect, the present invention provides a pharmaceutical composition, comprising:
(i) an active ingredient that is the antibody-drug conjugate according to the first aspect or a combination thereof; and
(ii) a pharmaceutically acceptable carrier.

In another preferred example, the pharmaceutical composition is an unit dosage form for human.

In another preferred example, the pharmaceutical composition is a liquid formulation.

In another preferred example, in the pharmaceutical composition, the antibody-drug conjugate is in an amount of 0.005-50 wt %, preferably 0.05-10 wt %.

In another preferred example, the pharmaceutical composition further comprises (iii) an additional therapeutic agent.

In another preferred example, the additional therapeutic agent includes a chemotherapeutic agent.

In the fourth aspect, the present invention provides a method for non-therapeutically inhibiting tumor cells in vitro, comprising the step of: contacting the tumor cells with the antibody-drug conjugate according to the first aspect.

In the fifth aspect, the present invention provides a method for treating a tumor, comprising the step of: administering to a subject in need thereof the antibody-drug conjugate according to the first aspect.

In another preferred example, the subject is a mammal, including human.

In another preferred example, the contacting is carried out in an in vitro culture system.

In the sixth aspect, the present invention provides a method for slowing tumor growth in a subject, comprising the step of: using an effective amount of the antibody-drug conjugate according to the first aspect in combination with one or more therapies selected from: radiation therapy, chemotherapy, biological therapy, or a combination thereof.

In the seventh aspect, the present invention provides a method for inhibiting cell migration in a subject, comprising the step of: using an effective amount of the antibody-drug conjugate according to the first aspect in combination with one or more therapies selected from: radiation therapy, chemotherapy, biological therapy, or a combination thereof.

In the eighth aspect, the present invention provides a method for inhibiting cell adhesion in a subject, comprising the step of: using an effective amount of the antibody-drug conjugate according to the first aspect in combination with one or more therapies selected from: radiation therapy, chemotherapy, biological therapy, or a combination thereof.

In the ninth aspect, the present invention provides a method for preparing a humanized or chimeric antibody, comprising the steps of:

after cloning the nucleotide sequence of a murine antibody variable region according to the present invention into an expression vector containing a human antibody constant region, expressing the human-mouse chimeric antibody by transfecting animal cells;

after cloning the nucleotide sequence of an antibody variable region comprising human FR region according to the present invention into an expression vector comprising a human antibody constant region, expressing the humanized antibody by transfecting animal cells.

In another preferred example, the antibody is a partially or fully humanized monoclonal antibody.

It should be understood that within the scope of the present invention, the above-mentioned technical features of the present invention and the technical features specifically described below (e.g. in Examples) may be combined with each other so as to constitute a new or preferred technical solution. For the purpose of space saving, these combinations are no longer described here.

SPECIFIC MODES FOR CARRYING OUT THE INVENTION

Figure 1:
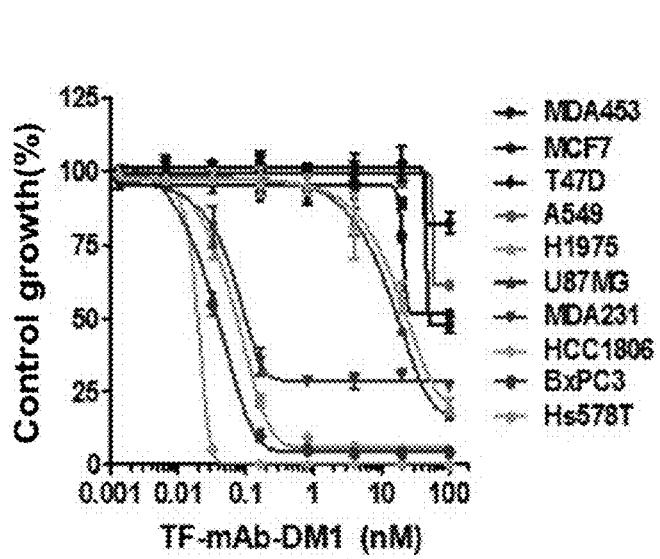
FIG. 1 shows that TF-mAb-DM1 could significantly inhibit the growth of tumor cells with high TF expression and the inhibition is proportional to TF molecules on the cell surface, wherein the left figure was the curve showing that TF-mAb-DM1 could well inhibit the growth of tumor cells with high TF expression, and the right table showed the $IC_{50}$ values of TF-mAb-DM1 for different cell lines.

The inventors obtain an anti-TF monoclonal antibody (TF-mAb-SC1) unexpectedly by conducting extensive and deep research and a large number of screening, and the experimental results show that the monoclonal antibody against TF protein is an IgG2b antibody. The antibody can bind to TF antigen with high specificity, and has high affinity (the $EC_{50}$ is about 0.019 nM as determined by ELISA), and the antibody has significant antitumor activity, and has no obvious toxic side-effects on mammals themselves. The chimeric antibody, the humanized antibody, and the corresponding ADC, which are obtained based on the TF-mAb-SC1, also have excellent characteristics. The present invention has been accomplished on the basis of these.

Terms

As used herein, the terms "antibody drug conjugate", "antibody conjugate", "antibody-drug conjugate", "antibody-drug conjugate" and "immunoconjugate" can be used interchangeably, and refer to the conjugate formed by (a) an antibody or an active fragment and (b) a drug.

As used herein, the terms "the antibody drug conjugate according to the present invention", "the antibody-drug conjugate according to the present invention" and "the ADC according to the present invention" can be used interchangeably, and refer to a conjugate formed by a drug and the antibody against tissue factor or an active fragment thereof according to present invention.

Unless otherwise defined, all the technical and scientific terms used herein have the same meaning as commonly understood by those skilled in the art. As used herein, the term "about", which is used when a particular value is mentioned, means that the value can vary by no more than 1% from the recited value. For example, the expression "about 100" includes all values between 99 and 101 (e.g. 99.1, 99.2, 99.3, 99.4, etc.).

Antibody

As used herein, the term "antibody" or "immunoglobulin" is a heterotetrameric glycoprotein of about 150,000 Da having the same structural characteristics, which consists of two identical light chains (L) and two identical heavy chains (H). Each light chain is linked to a heavy chain via a covalent disulfide bond, and different immunoglobulin isotypes have different numbers of disulfide bonds between the heavy chains. There are also regularly spaced intrachain disulfide bonds in each heavy and each light chain. Each heavy chain has a variable region (VH) at one end, followed by a plurality of constant regions. Each light chain has a variable region (VL) at one end and a constant region at the other end; the constant region of a light chain pairs with the first constant region of a heavy chain, and the variable region of a light chain pairs with the variable region of a heavy chain. Special amino acid residues form an interface between the variable regions of a light chain and a heavy chain.

As used herein, the term "variable" means that antibodies are different from each other in terms of sequence in certain parts of variable regions, which is responsible for the binding and specificity of various specific antibodies to their specific antigens. However, the variability is not distributed evenly throughout the variable regions of an antibody. It is concentrated in three segments called complementarity determining regions (CDRs) or hypervariable regions in the light and heavy chain variable regions. The conserved parts of variable regions are called framework regions (FRs). Each of the variable regions of naturally occurring heavy and light chains comprises four FR regions, which are generally in a β-sheet configuration, joined by the three CDRs forming a linking loop, and in some cases, may form a partial β-sheet structure. The CDRs in each chain are closely linked together via the FR regions, and together with the CDRs of the other chain, form the antigen binding site of an antibody (see Kabat et al., NIH Publ. No. 91-3242, Vol. I, pp. 647-669 (1991)). The constant regions are not directly involved in the binding of an antibody to an antigen, however, they exhibit different effector functions, for example, they are involved in the antibody-dependent cytotoxicities of an antibody.

The "light chain" of a vertebrate antibody (immunoglobulin) can be classified into one of the two obviously different classes (referred to as κ and λ) depending on the amino acid sequence of its constant region. Immunoglobulins can be classified into different classes depending on the amino acid sequences of their heavy chain constant regions. There are mainly five classes of immunoglobulins: IgA, IgD, IgE, IgG, and IgM, some of which can be further classified into subclasses (isotypes), such as IgG1, IgG2, IgG3, IgG4, IgA, and IgA2. The heavy chain constant regions corresponding to different classes of immunoglobulins are called α, δ, ε, γ, and μ, respectively. The subunit structures and three-dimensional configurations of different classes of immunoglobulins are well known for those skilled in the art.

In general, the antigen binding characteristics of an antibody can be described by three specific regions located in the heavy and light chain variable regions, called complementarity determining regions (CDRs), which divide the variable region into four framework regions (FRs); the amino acid sequences of the four FR are relatively conservative and are not directly involved in the binding reaction. These CDRs form a ring structure, and approach to each other in the steric structure by virtue of the β-sheets formed by the FRs between them, and the CDRs on the heavy chain and the CDRs on the corresponding light chain constitute the antigen-binding site of an antibody. By comparison of the amino acid sequences of antibodies of the same type, it can be determined which amino acids form FRs or CDRs.

The present invention includes not only an intact antibody, but also the fragments of the antibody having an immunological activity or a fusion protein formed by the antibody and another sequence. Therefore, the present invention also includes fragments, derivatives and analogs of the antibody.

In the present invention, antibodies include murine, chimeric, humanized or fully human antibodies as prepared by techniques well known to those skilled in the art. Recombinant antibodies, such as chimeric and humanized monoclonal antibodies, including human and non-human portions, can be obtained by standard DNA recombination techniques, all of which are useful antibodies. A chimeric antibody is a molecule in which different portions are derived from different animal species, for example, a chimeric antibody having a variable region from a monoclonal antibody from a mouse, and a constant region from a human immunoglobulin (see, for example, U.S. Pat. Nos. 4,816,567 and 4,816,397, which are incorporated herein by reference in its entirety). A humanized antibody refers to an antibody molecule derived from a non-human species, which has one or more complementarity determining regions (CDRs) derived from a non-human species and framework regions derived from a human immunoglobulin molecule (see U.S. Pat. No. 5,585,089, which is incorporated herein by reference in its entirety). These chimeric and humanized monoclonal antibodies can be prepared by recombinant DNA techniques well known in the art.

In the present invention, an antibody may be monospecific, bispecific, trispecific, or multispecific.

In the present invention, the antibody according to the present invention further include a conservative variant thereof, which refers to a polypeptide formed by substitution of at most 10, preferably at most 8, more preferably at most 5, and most preferably at most 3 amino acids with similar amino acids, as compared to the amino acid sequence of the antibody according to the present invention. These conservative variant polypeptide is preferably prepared by the amino acid substitution according to Table A.

TABLE A

| Initial residue | Representative substitution | Preferred substitution |
|---|---|---|
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Be; Leu; Met; Phe; Ala | Leu |

Anti-TF Antibodies of the Present Invention

The present invention provides an antibody having high specificity and high affinity to TF, comprising a heavy chain and a light chain, wherein the heavy chain comprises the amino acid sequence of a heavy chain variable region (VH), and the light chain comprises the amino acid sequence of a light chain variable region (VL).

Preferably, the CDRs for the amino acid sequence of the heavy chain variable region (VH) and the amino acid sequence of the light chain variable region (VL) are selected from the group consisting of:
   a1) SEQ ID No:1;
   a2) SEQ ID No:2;
   a3) SEQ ID No:3;
   a4) SEQ ID No:4;
   a5) SEQ ID No:5;
   a6) SEQ ID No:6;
   a7) a sequence that is optionally resulted from the addition, deletion, modification and/or substitution of at least one amino acid of any amino acid sequence of said amino acid sequences, and has TF-binding affinity.

In another preferred example, the sequence resulted from the addition, deletion, modification and/or substitution of at least amino acid is preferably an amino acid sequence having a homology of at least 80%, preferably at least 85%, more preferably at least 90%, most preferably at least 95%.

Preferably, the antibody has the activity of inhibiting the TF-related signal pathway; has an anticoagulant activity; has an activity of inhibiting FXa production, or a combination thereof.

Typically, the present invention provides an anti-TF antibody having: the heavy chain variable region according to the present invention; and/or the light chain variable region according to the present invention;
   wherein, the heavy chain variable region of the antibody comprises the following three complementary determining regions (CDRs):
   CDR1 as set forth in SEQ ID NO:1,
   CDR2 as set forth in SEQ ID NO:2, and
   CDR3 as set forth in SEQ ID NO:3;
   wherein any amino acid sequence of said amino acid sequences further includes a derivative sequence that is optionally resulted from the addition, deletion, modification and/or substitution of at least one amino acid, and can retain a TF-binding activity;
   the light chain variable region of the antibody comprises the following three complementary determining regions (CDRs):
   CDR1' as set forth in SEQ ID NO:4,
   CDR2' as set forth in SEQ ID NO:5, and
   CDR3' as set forth in SEQ ID NO:6;
   wherein any amino acid sequence of said amino acid sequences is a derivative sequence that is resulted from the addition, deletion, modification and/or substitution of at least one amino acid, and has a TF-binding activity.

Preferably, the heavy chain variable region of the antibody is selected from: SEQ ID NO: 7, 9, 10, 11, 12, or 13; and/or the light chain variable region of the antibody is selected from: SEQ ID NO: 8, 14, 15, 16, or 17.

In the present invention, the antibody is selected from: an animal-derived antibody, a chimeric antibody, a humanized antibody, or a combination thereof. In another preferred example, the number of the added, deleted, modified and/or substituted amino acids does not exceed 40% of the total number of the amino acids of the initial amino acid sequence.

In another preferred example, the number of the added, deleted, modified and/or substituted amino acids is 1-7.

In another preferred example, the sequence resulted from the addition, deletion, modification and/or substitution of at least one amino acid is an amino acid sequence having a homology of at least 80%.

In another preferred example, the sequence resulted from the addition, deletion, modification and/or substitution of at least one amino acid has one or more of an activity of inhibiting TF-related signal pathway, an anticoagulant activity, and an activity of inhibiting FXa production.

The antibody according to the present invention may be a double-chain or single-chain antibody, and may be selected from the group consisting of an animal-derived antibody, a chimeric antibody, and a humanized antibody; more preferably, may be selected from the group consisting of a humanized antibody, and a human-animal chimeric antibody; and more preferably, may be a fully human antibody.

The antibody derivative according to the present invention may be a single-chain antibody, and/or an antibody fragment, for example, Fab, Fab', (Fab')2 or other antibody derivatives known in the art, etc., and may be any one or more of IgA, IgD, IgE, IgG and IgM antibodies or other subtype antibodies.

In the present invention, the animal is preferably a mammal, such as mouse.

The antibody according to the present invention may be a chimeric antibody targeted to human TF, a humanized antibody, a CDR grafted and/or modified antibody.

In a preferred example of the present invention, any one or more sequences of SEQ ID No: 1 to SEQ ID No: 3, or sequences thereof that are resulted from the addition, deletion, modification and/or substitution of at least one amino acid and have a TF-binding affinity, are located in the CDRs of heavy chain variable region (VH).

In a preferred example of the present invention, any one or more sequences of SEQ ID No: 4 to SEQ ID No: 6, or sequences thereof that are resulted from the addition, deletion, modification and/or substitution of at least one amino acid and have a TF-binding affinity, are located in the CDRs of light chain variable region (VL).

In a more preferred example of the present invention, VH CDR1, CDR2, CDR3 are independently selected from any one or more sequences of SEQ ID No: 1 to SEQ ID No: 3, or sequences thereof that are resulted from the addition, deletion, modification and/or substitution of at least one amino acid and have a TF-binding affinity; VL CDR1, CDR2, CDR3 are independently selected from any one or more sequences of SEQ ID No: 4 to SEQ ID No: 6, or sequences thereof that are resulted from the addition, deletion, modification and/or substitution of at least one amino acid and have a TF-binding affinity.

In the present invention, the number of the added, deleted, modified and/or substituted amino acids, preferably does not exceed 40%, more preferably does not exceed 35%, is more preferably 1-33%, is more preferably 5-30%, is more preferably 10-25%, and is more preferably 15-20% of the total number of the amino acids of the initial amino acid sequence.

In the present invention, more preferably, the number of the added, deleted, modified and/or substituted amino acids, may be 1-7, more preferably 1-5, more preferably 1-3, more preferably 1-2.

In another preferred example, the antibody targeted to TF is TF-mAb-SC1 (the original name of which is TF-mAb).

In another preferred example, the amino acid sequence of the heavy chain variable region (VH) of the antibody TF-mAb-SC1 is the amino acid sequence as set forth in SEQ ID NO: 7.

In another preferred example, the amino acid sequence of the light chain variable region (V-Kappa) of the antibody TF-mAb-SC1 is the amino acid sequence as set forth in SEQ ID NO: 8.

Preparation of Antibodies

The sequence of the DNA molecule for the antibody or a fragment thereof according to the present invention can be obtained by conventional techniques, for example, methods such as PCR amplification or genomic library screening. In addition, the sequences encoding light chain and heavy chain can be fused together, to form a single-chain antibody.

Once a relevant sequence is obtained, recombination methods can be used to obtain the relevant sequence in large quantities. This is usually carried out by cloning the sequence into a vector, transforming a cell with the vector, and then separating the relevant sequence from the proliferated host cell by conventional methods.

In addition, a relevant sequence can be synthesized artificially, especially when the fragment is short in length. Usually, several small fragments are synthesized first, and then are linked together to obtain a fragment with a long sequence.

It has been possible now to obtain a DNA sequence encoding the antibody (or a fragment thereof, or a derivative thereof) according to the present invention completely by chemical synthesis. Then, the DNA sequence can be introduced into various existing DNA molecules (or, for example, vectors) and cells known in the art. In addition, mutations can also be introduced into the protein sequence according to the present invention by chemical synthesis.

The present invention further relates to a vector comprising said suitable DNA sequence and a suitable promoter or a control sequence. These vectors can be used to transform suitable host cells to enable them to express protein.

The host cell can be a prokaryotic cell, such as a bacterial cell; or a lower eukaryotic cell, such as a yeast cell; or a higher eukaryotic cell, such as a mammalian cell. Preferred animal cells include, but are not limited to, CHO-S, HEK-293 cells.

In general, under conditions suitable for expression of the antibody according to the present invention, the host cell obtained is cultured. Then, the antibody according to the present invention is purified by using conventional immunoglobulin purification steps, for example, the conventional separation and purification means well known to those skilled in the art, such as protein A-Sepharose, hydroxyapatite chromatography, gel electrophoresis, dialysis, ion exchange chromatography, hydrophobic chromatography, molecular sieve chromatography or affinity chromatography.

The monoclonal antibody obtained can be identified by conventional means. For example, the binding specificity of a monoclonal antibody can be determined by immunoprecipitation or an in vitro binding assay (such as radioimmunoassay (RIA) or enzyme-linked immunosorbent assay (ELISA)). The binding affinity of a monoclonal antibody can be determined by, for example, the Scatchard analysis (Munson et al., Anal. Biochem., 107: 220 (1980)).

The antibody according to the present invention can be expressed in a cell or on the cell membrane, or is secreted extracellularly. If necessary, the recombinant protein can be separated and purified by various separation methods according to its physical, chemical, and other properties. These methods are well known to those skilled in the art. Examples of these methods include, but are not limited to, conventional renaturation treatment, treatment with a protein precipitant (salting out method), centrifugation, osmotic bacteria disruption, ultrasonic treatment, ultracentrifugation, molecular sieve chromatography (gel filtration), adsorption chromatography, ion exchange chromatography, high performance liquid chromatography (HPLC), various other liquid chromatographic techniques, and combinations of these methods.

Cytotoxic Agents

Drugs, which can be used to form the ADC according to the present invention, include, but are not limited to: cytotoxic agents.

The term "cytotoxic agents" refer to substances that inhibit or block cell expression activity, cell function and/or result in cell destruction. The term includes radioisotopes, chemotherapeutics, and toxins, such as small-molecular toxins or enzymatically active toxins (including fragments and/or variants thereof) derived from bacteria, fungi, plants or animals. Examples of cytotoxic agents include, but are not limited to: auristatins (e.g. auristatin E, auristatin F, MMAE and MMAF), chlortetracycline, maytansinols, ricin, ricin A-chain, cobstatin, duocarmycin, dolastatin, doxorubicin, daunorubicin, paclitaxel, cisplatin, cc1065, ethidium bromide, mitomycin, etoposide, tenoposide, vincristine, vinblastine, colchicine, dihydroxy anthrax dione, actinomycin, diphtheria toxin, Pseudomonas exotoxin (PE) A, PE40, Acacia toxin, Acacia toxin A chain, modeccin A chain, α-sarcina, gelonin, mitogellin, retstrictocin, phenomycin, enomycin, curicin, crotin, calicheamicin, Sapaonaria officinalis inhibitor, glucocorticoid and other chemotherapeutic agents, as well as radioisotopes such as At211, I131, I125, Y90, Re186, Re188, Sm153, Bi212 or 213, P32 and the radioisotopes of Lu including Lu177. An antibody can also be conjugated to an anti-cancer prodrug-activating enzyme that can convert the prodrug into its active form.

A preferred small-molecule drug is a compound having high cytotoxicity, preferably monomethyl auristatin, calicheamicin, maytansines, or a combination thereof; more preferably is selected from: monomethyl auristatin E (MMAE), monomethyl auristatin-D (MMAD), monomethyl auristatin-F (MMAF), or a combination thereof.

Antibody-Drug Conjugate (ADC)

The present invention also provides an antibody-drug conjugate (ADC) based on the antibody according to the present invention.

Typically, the antibody-drug conjugate comprises the antibody and an effector molecule, wherein the antibody is conjugated to the effector molecule, and chemical conjugation is preferred. Preferably, the effector molecule is a therapeutically active drug. In addition, the effector molecule may be one or more of a toxic protein, a chemotherapeutic drug, a small-molecule drug or a radionuclide.

The antibody according to present invention and the effector molecule may be coupled by a coupling agent. Examples of the coupling agent may be any one or more of a non-selective coupling agent, a coupling agent utilizing a carboxyl group, a peptide chain, and a coupling agent utilizing a disulfide bond. The non-selective coupling agent refers to a compound that results in a linkage between an effector molecule and an antibody via a covalent bond, such as glutaraldehyde, etc. The coupling agent utilizing a carboxyl group may be any one or more of cis-aconitic anhydride coupling agents (such as cis-aconitic anhydride) and acyl hydrazone coupling agents (the coupling site is acyl hydrazone).

Certain residues on an antibody (such as Cys or Lys, etc.) are used to link a variety of functional groups, including imaging agents (such as chromophores and fluorophores), diagnostic agents (such as MRI contrast agents and radioisotopes), stabilizers (such as poly(ethylene glycol)) and therapeutic agents. An antibody can be conjugated to a functional agent to form a conjugate of the antibody-functional agent. A functional agent (e.g. a drug, a detection reagent, a stabilizer) is conjugated (covalently linked) to an antibody. A functional agent can be linked to an antibody either directly or indirectly via a linker.

Typical conjugation manners suitable for the present invention include both K-Lock and C-Lock conjugation manners. In the K-Lock conjugation manner, a drug molecule is conjugated to the lysine (K) residue in an antibody sequence; in the C-Lock conjugation manner, a drug molecule is coupled to the cysteine (C) residue in an antibody sequence.

Antibodies can be conjugated to drugs to form antibody-drug conjugates (ADCs). Typically, an ADC comprises a linker between a drug and an antibody. The linker can be a degradable or non-degradable linker. Typically, degradable linkers are easily degraded in an intracellular environment, for example, the linker is degraded at the target site, thereby releasing the drug from the antibody. Suitable degradable linkers include, for example, enzyme-degradable linkers, including peptidyl-containing linkers that can be degraded by protease (e.g. lysosomal protease or endosomal protease) in a cell, or sugar linkers, for example, glucuronide-containing linkers that can be degraded by glucuronidase. Peptidyl linkers may include, for example, dipeptides, such as valine-citrulline, phenylalanine-lysine or valine-alanine. Other suitable degradable linkers include, for example, pH sensitive linkers (e.g. linkers that are hydrolyzed at a pH of below 5.5, such as hydrazone linkers) and linkers that are degraded under reducing conditions (e.g. disulfide-bond linkers). A non-degradable linker typically releases a drug under conditions that the antibody is hydrolyzed by protease.

Prior to linkage to an antibody, a linker has a reactive group capable of reacting with certain amino acid residues, and the linkage is achieved by the reactive group. A thiol-specific reactive group is preferred, and includes, for example, a maleimide compound, a halogenated (e.g. iodo-, bromo- or chloro-substituted) amide; a halogenated (e.g. iodo-, bromo- or chloro-substituted) ester; a halogenated (e.g. iodo-, bromo- or chloro-substituted) methyl ketone, a benzyl halide (e.g. iodide, bromide or chloride); vinyl sulfone, pyridyl disulfide; a mercury derivative such as 3,6-di-(mercurymethyl)dioxane, wherein the counter ion is $CH_3COO^-$, $Cl^-$ or $NO_3^-$; and polymethylene dimethyl sulfide thiosulfonate. The linker may include, for example, a maleimide linked to an antibody via thiosuccimide.

A drug may be any cytotoxic, cytostatic or immunosuppressive drug. In an embodiment, an antibody is linked to a drug via a linker, and the drug has a functional group that can form a bond with the linker. For example, a drug may have an amino group, a carboxyl group, a thiol group, a hydroxyl group, or a ketone group that can form a bond with a linker. When a drug is directly linked to a linker, the drug has a reactive group before being linked to an antibody.

Useful drugs include, for example, anti-tubulin drugs, DNA minor groove binding agents, DNA replication inhibitors, alkylating agents, antibiotics, folic acid antagonists, antimetabolites, chemotherapy sensitizers, topoisomerase inhibitors, vinca alkaloids, etc. Examples of particularly useful cytotoxic drugs include, for example, DNA minor groove binding agents, DNA alkylating agents, and tubulin inhibitors; typical cytotoxic drugs include, for example, auristatins, camptothecins, docamycin/duocarmycins, etoposides, maytansines and maytansinoids (e.g. DM1 and DM4), taxanes, benzodiazepines or benzodiazepine containing drugs (e.g. pyrrolo[1,4]benzodiazepines (PBDs), indolinobenzodiazepines and oxazolidinobenzodiazepines), and vinca alkaloids.

In the present invention, a drug-linker can be used to form an ADC in a simple step. In other embodiments, a bifunctional linker compound can be used to form an ADC in a two-step or multi-step process. For example, a cysteine residue is reacted with the reactive moiety of a linker in a first step, and then the functional group on the linker is reacted with a drug in the subsequent step, so as to form an ADC.

In general, the functional group on a linker is selected so that it can specifically react with the suitable reactive group on a drug moiety. As a non-limiting example, an azide-based moiety can be used to specifically react with the reactive alkynyl group on a drug moiety. The drug is covalently bound to the linker by 1,3-dipolar cycloaddition between the azide and alkynyl group. Other useful functional groups include, for example, ketones and aldehydes (suitable for reacting with hydrazides and alkoxyamines), phosphines (suitable for reacting with azides); isocyanates and isothiocyanates (suitable for reacting with amines and alcohols); and activated esters, for example, N-hydroxysuccinimide esters (suitable for reacting with amines and alcohols). These and other linkage strategies, for example, those described in Bioconjugation Technology ($2^{nd}$ Edition (Elsevier)), are well known to those skilled in the art. Those skilled in the art could understand that when a complementary pair of reactive functional groups are selected for a selective reaction between a drug moiety and a linker, each member of the complementary pair can be used for the linker, and can also be used for the drug.

The present invention further provides a method for preparing an ADC, which may further comprise: under conditions sufficient to form an antibody-drug conjugate (ADC), binding an antibody to a drug-linker compound.

In certain embodiments, the method according to the present invention comprises: under conditions sufficient to form an antibody-linker conjugate, binding an antibody to a bifunctional linker compound. In these embodiments, the method according to the present invention further comprises: under conditions sufficient to covalently link the drug moiety to the antibody via a linker, binding the antibody-linker conjugate to the drug moiety.

In some embodiments, an antibody-drug conjugate (ADC) has a formula as follows:

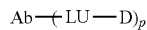

wherein:
Ab is an antibody,
LU is a linker;
D is a drug;
and the subscript p is an value selected from 1 to 10, preferably from 1 to 8.

Application

The present invention further provides use of the antibody according to the present invention, for example, for manufacture of a diagnostic agent, or for manufacture of a medicament for preventing and/or treating a TF-related disease. The TF-related disease includes tumorigenesis, tumor growth and/or metastasis, a thrombosis-related disease, inflammation, a metabolism-related disease, etc.

Use of the antibody, ADC or CAR-T according to the present invention includes (but is not limited to):

(i) for diagnosis, prevention and/or treatment of tumorigenesis, tumor growth and/or metastasis, particularly, a tumor with high TF expression, wherein the tumor includes (but is not limited to): breast cancer (e.g. triple-negative breast cancer), pancreatic cancer, lung cancer, malignant glioma, gastric cancer, liver cancer, esophageal cancer, kidney cancer, colorectal cancer, bladder cancer, prostate cancer, endometrial cancer, ovarian cancer, cervical cancer, leukemia, bone marrow cancer, angiosarcoma, etc.; particularly, triple negative breast cancer, pancreatic cancer, malignant glioma and lung cancer; more preferably triple negative breast cancer and/or pancreatic cancer;

(ii) for diagnosis, prevention and/or treatment of a thrombosis-related disease, wherein the thrombosis-related diseases includes (but is not limited to): atherosclerosis, acute coronary syndrome, acute myocardial infarction, stroke, hypertension, deep vein thrombosis, pulmonary embolism, renal embolism and arterial surgery, thrombosis caused by coronary artery bypass grafting, etc.;

(iii) for diagnosis, prevention and/or treatment of inflammation, wherein the inflammation includes (but is not limited to): rheumatic arthritis, osteoarthritis, ankylosing spondylitis, gout, Lytle syndrome, psoriasis arthritis, infectious arthritis, tuberculous arthritis, viral arthritis, fungal arthritis, glomerular Nephritis, systemic lupus erythematosus, Crohn's disease, ulcerative colitis, acute lung injury, chronic obstructive pulmonary disease, and idiopathic pulmonary fibrosis;

(iv) for diagnosis, prevention and/or treatment of a metabolism-related disease, wherein the metabolism-related disease includes (but is not limited to): diabetes, diet-induced obesity, adipose inflammation, etc.

Pharmaceutical Composition

The present invention further provides a composition. In the preferred examples, the composition is a pharmaceutical composition comprising the antibody, or an active fragment, a fusion protein or an ADC thereof, or a corresponding CAR-T cell, and a pharmaceutically acceptable carrier. In general, these substances may be formulated in a non-toxic, inert and pharmaceutically acceptable aqueous carrier medium, wherein the pH is generally about 5-8, preferably, pH is about 6-8, though the pH value may be varied depending on the nature of the substances to be formulated and the condition to be treated. The formulated pharmaceutical composition may be administered by conventional routes, including (but not limited to): intratumoral, intraperitoneal, intravenous, or topical administration.

The pharmaceutical composition according to the present invention can be directly used for binding to a TF protein molecule, and thus can be used for preventing and treating diseases such as tumors. In addition, other therapeutic agents can be used simultaneously, for example, various cytokines such as TNF, IFN, IL-2, etc.; various chemotherapeutics for tumors, for example, drugs that affect biosynthesis of nucleic acids, such as 5-FU and methotrexate; alkylating agents such as nitrogen mustard and cyclophosphamide;

drugs that interfere transcription and block RNA synthesis, such as doxorubicin and actinomycin D; vincristine, camptothecin.

The pharmaceutical composition according to the present invention comprises a safe and effective amount (e.g. 0.001-99 wt %, preferably 0.01-90 wt %, preferably 0.1-80 wt %) of the monoclonal antibody according to the present invention (or a conjugate thereof) and a pharmaceutically acceptable carrier or excipient. Such carriers include (but are not limited to): saline, buffers, glucose, water, glycerol, ethanol, and a combination thereof. Pharmaceutical preparations should correspond to the administration modes. The pharmaceutical composition according to the present invention can be prepared in the form of an injection, for example, by a conventional method using physiological saline or an aqueous solution containing glucose and other adjuvants. A pharmaceutical composition, for example, an injection and a solution, should be prepared under aseptic conditions. The administration amount of an active ingredient is a therapeutically effective amount, for example, about 1 μg per kilogram of body weight to about 5 mg per kilogram of body weight daily. In addition, the polypeptide according to the present invention may also be used in combination with an additional therapeutic agent.

When a pharmaceutical composition is used, a safe and effective amount of an immunoconjugate is administered to a mammal, wherein the safe and effective amount is generally at least about 10 μg per kilogram of body weight, and in most cases, no more than about 50 mg per kilogram of body weight, Preferably, the amount is from about 10 μg per kilogram of body weight to about 20 mg per kilogram of body weight. Of course, a specific amount should also depend on the factors such as administration route and physical conditions of a patient, which fall into the skills of skilled physicians.

The main advantages of the present invention include:
(a) the antibody according to the present invention has excellent bioactivity and specificity, and has very high affinity (the $EC_{50}$ may reach approximately 0.01-0.03 nM as determined by ELISA); in addition, it has good binding affinity for cell surface TF, and may be used as an TF-targeting antibody;
(b) the humanized antibody according to the present invention not only has an activity comparable to that of immune antibodies, but also has a lower immunogenicity;
(c) both the antibody and the ADC according to the present invention have a significant anti-tumor activity, and have no obvious toxic side-effects on mammals themselves; and
(d) the antibody and the ADC according to the present invention not only have significant therapeutic effects in tumor models, but also are applicable to other high TF expression-associated diseases.

The present invention is further described by reference to the following particular examples. It should be understood that the following examples are only used to describe the present invention, rather than limiting the scope of the present invention. The experimental methods in the following examples, the specific conditions of which are not indicated, are usually carried out according to conventional conditions, for example, the conditions described in Sambrook et al., Molecular Cloning: Laboratory Manual (New York: Cold Spring Harbor Laboratory Press, 1989), or the conditions recommended by the manufacturers. Unless otherwise specified, percentages and parts refer to percentages by weight and parts by weight, respectively. Cell lines are the conventional products that are commercially available or are purchased from ATCC, and all the plasmids are the commercially available products.

Example 1 Discovery and Preparation of Monoclonal Antibodies Targeted to Human TF Step ①, Preparation of Hybridoma Cells:

Firstly, 8-week old Balb/c female mice were immunized with the extracellular domain of human TF protein (UniProtKB/Swiss-Prot: P13726.1, the amino acids from positions 34 to 251), wherein the extracellular domain protein of TF was used in an amount of 100 μg/mouse, to prepare the immunized splenocytes; murine myeloma cells (SP2/0) and feeder cells were prepared at an appropriate time in case of fusion.

After said three kinds of cells were prepared, the fusion of splenocytes with SP2/0 cells was mediated by PEG, PEG was removed, and the resultant cells were re-suspended in HAT complete medium containing feeder cells, and were seeded and cultured in a 96-well plate. Positive wells were screened by ELISA. Finally, the cells in the positive wells were subjected to clonal culture by limiting dilution method, and the cells, which had a high titer, were in a good morphology and grew in a monoclonal manner, were screened by ELISA or immunofluorescence technique. The cells grew in a monoclonal manner were further subjected to subcloning screening until the positive cloning rate was 100% for three consecutive screening. After which, the cell line could be subjected to amplification and library construction.

Step ②, Preparation of the Ascites of Murine Monoclonal Antibodies Targeted to Human TF:

The hybridoma cells screened out in Step ① were subjected to amplification. After adaptive raising, pristane (0.5 mL/mouse) was injected into the abdominal cavity of mice so as to provide a favorable environment for the growth of hybridoma cells. 7-10 days later, $10 \times 10^6$ hybridoma cells were injected into the abdominal cavity of each mouse. The mice were observed everyday for their production of ascites and their mental states since the seventh day, and the ascites was collected, centrifuged to remove fats, and cryopreserved at −80° C. for purification in the next step.

Step ③, Purification of Murine Monoclonal Antibodies Targeted to Human TF:

The ascites cryopreserved in Step ② was thawed on ice, and was dialyzed with PBS at 4° C. overnight after filtration through a 0.45 μm filter. Finally, the antibody was purified by FPLC technique, subjected to ultrafiltration, concentrated to the desired concentration, sub-packaged and cryopreserved at −80° C. for further use.

Step ④, Determination of the Bioactivity and Targeting Specificity of Murine Monoclonal Antibodies Targeted to Human TF:

After preliminary screening, about 30 hybridoma cells were selected for secondary limiting dilution cloning, and then 6 antibodies were selected for large-scale expression and purification. Each antibody was determined at a concentration of 10 μg/mL by flow cytometry for its affinity to human breast cancer cell MDA-MB-231, human pancreatic cancer cell BxPC-3 and murine melanoma cell B16-F10.

The result showed that the antibodies tested could specifically bind to human TF (MDA-MB-231 and BxPC-3 cells) without specifically binding to murine TF (B16-F10 cells), wherein TF-mAb-SC1 had a higher affinity for human TF than the other 5 antibodies.

Later, the ELISA plate was coated with the extracellular domain protein of TF at 0.05 μg/well in the ELISA assay. The result showed that TF-mAb-SC1 had a strong binding affinity to the extracellular domain protein of TF; the cell binding affinity assay showed that TF-mAb-SC1 had a very high affinity for triple-negative breast cancer cells (MDA-MB-231), and pancreatic cancer cells (BxPC-3) with high TF expression; and TF-mAb-SC1 could significantly inhibit the phosphorylation level of TF-PAR2 downstream MAPK/ERK with a certain degree of dose-dependency.

Since TF-mAb-SC1 exhibited a very high specificity, a very high affinity and a significant inhibitory effect on the phosphorylation level of MAPK/ERK, it was selected for sequencing and subsequent studies.

By conventional sequencing and analysis according to Kabat database, the following sequence information was obtained.

The amino acid sequences of the CDRs of the heavy chain variable region were:

```
SEQ ID No: 1:
SYWMN;

SEQ ID No: 2:
MIYPADSETRLNQKFKD;

SEQ ID No: 3:
EDYGSSDY.
```

The complete VH amino acid sequence was as set forth in SEQ ID NO: 7.

(SEQ ID NO: 7)
QVQLQQPGAELVRPGASVKLSCKASGYSFISYWMNWVKQRPGQGLEWIG

MIYPADSETRLNQKFKDKATLTVDKSSSTAYMQLSSPTSEDSAVYYCAR

EDYGSSDYWGQGTTLTVSS

The amino acid sequences of the CDRs of the light chain variable region were:

```
SEQ ID No: 4:
SASSSVSYMN;

SEQ ID No: 5:
GISNLAS;

SEQ ID No: 6:
QQKSSFPWT.
```

The complete VL amino acid sequence was as set forth in SEQ ID NO: 8:

(SEQ ID NO: 8)
EILLTQSPAIIAASPGEKVTITCSASSSVSYMNWYLQKPGSSPKIWIYG

ISNLASGVPARFSGSGSGTSFSFTINSMETEDVATYYCQQKSSFPWTFG

GGTKLEIK

Example 2 Preparation of a Human-Mouse Chimeric Antibody

A human-mouse chimeric antibody was constructed after obtaining the highly active and specific murine TF-mAb-SC1 antibody.

Primers were designed to introduce EcoR I and Nhe I into the heavy chain variable region, and to introduce the Age I and BsiW I restriction endonuclease sites into the light chain variable region, and then the sequences of the heavy chain and light chain variable region of the antibody obtained above were separately cloned into the vectors containing the heavy chain constant region and the Kappa chain constant region of human IgG1. After confirmation by identification, the constructed chimeric antibody was expressed and purified by using transfection technique and mammalian expression systems (CHO-S or HEK-293 cells), and the human-mouse chimeric antibody obtained was designated as TF-mAb-Ch.

Example 3 Humanization of TF-mAb-SC1 and Determination of Activity

By reference to the sequences of the heavy chain variable region (SEQ ID NO: 7) and the light chain variable region (SEQ ID NO: 8) of the TF-mAb-SC1 antibody, the humanized template, which matched the non-CDR regions best, was selected from the Germline database. The CDR regions of the murine antibody TF-mAb-SC1 were then grafted to the humanized template selected, so as to replace the CDR regions of the humanized template, followed by recombination with the IgG1/kappa constant region. Meanwhile, based on the three-dimensional structure of the murine antibody, back mutation was performed to the residues that were directly interacted with the CDR regions, and to the residues that had an important effect on the conformation of VL and VH, thereby obtaining 5 humanized heavy chain variable regions (SEQ ID NO: 9, SEQ ID NO: 10, SEQ ID NO: 11, SEQ ID NO: 12, and SEQ ID NO: 13) and 4 humanized light chain variable regions (SEQ ID NO: 14, SEQ ID NO: 15, SEQ ID NO: 16, and SEQ ID NO: 17).

TABLE B

| SEQ ID NO: | Sequence | Variable region |
|---|---|---|
| 9 | EVQLVQSGAEVKKPGESLKISCKGSGYSFTSY WMNWVRQMPGKGLEWMGMIYPADSETRLNQKF KDQATLSVDKSISTAYLQWSSLKASDTAMYYC AREDYGSSDYWGQGTTVTVSS | VH |
| 10 | EVQLVQSGAEVKKPGESLKISCKGSGYSFTSY WMNWVRQMPGKGLEWMGMIYPADSETRLNQKF KDKATLSVDKSISTAYLQWSSLKASDTAMYYC AREDYGSSDYWGQGTTVTVSS | VH |
| 11 | EVQLVQSGAEVKKPGESLKISCKGSGYSFTSY WMNWVKQMPGKGLEWMGMIYPADSETRLNQKF KDKATLSVDKSISTAYLQWSSLKASDTAMYYC AREDYGSSDYWGQGTTVTVSS | VH |
| 12 | QVQLVQSGAEVKKPGASVKVSCKASGYSFISY WMNWVRQAPGQGLEWIGMIYPADSETRLNQKF KDRATLTVDKSTSTAYMELSSLRSEDTAVYYC AREDYGSSDYWGQGTTVTVSS | VH |
| 13 | QVQLVQSGSELKKPGASVKVSCKASGYSFISY WMNWVRQAPGQGLEWIGMIYPADSETRLNQKF KDRAVLSVDKSVSTAYLQICSLKAEDTAVYYC AREDYGSSDYWGQGTTVTVSS | VH |
| 14 | EIVLTQSPATLSLSPGERATLSCSASSSVSYM NWYQQKPGQAPRIWIYGISNLASGIPARFSGS GSGTDFTLTISSLEPEDFAVYYCQQKSSFPWT FGGGTKVEIK | VL |
| 15 | EIVLTQSPATLSLSPGERATLSCSASSSVSYM NWYQQKPGQSPRIWIYGISNLASGVPARFSGS GSGTDFTLTISSLEPEDFAVYYCQQKSSFPWT FGGGTKVEIK | VL |

TABLE B-continued

| SEQ ID NO: | Sequence | Variable region |
|---|---|---|
| 16 | DIQLTQSPSSLSASVGDRVTITCSASSSVSYM NWYQQKPGKSPKIWIYGISNLASGVPSRFSGS GSGTDFTLTISSLQPEDFATYYCQQKSSFPWT FGGGTKVEIK | VL |
| 17 | EIVLTQSPDFQSVTPKEKVTITCSASSSVSYM NWYQQKPDQSPKIWIYGISNLASGVPSRFSGS GSGTDFTLTINSLEAEDAATYYCQQKSSFPWT FGGGTKVEIK | VL |

Based on the engineered VH and VL, these humanized heavy and light chains were separately expressed in combination to finally obtain 20 humanized antibodies in total, i.e. TF-mAb-H29 to TF-mAb-H48. The corresponding combinations of heavy chain and light chain for each antibody were shown in the following table:

TABLE C

| Sequence No. | SEQ ID NO: 9 | SEQ ID NO: 10 | SEQ ID NO: 11 | SEQ ID NO: 12 | SEQ ID NO: 13 |
|---|---|---|---|---|---|
| SEQ ID NO: 14 | TF-mAb-H29 | TF-mAb-H30 | TF-mAb-H31 | TF-mAb-H32 | TF-mAb-H33 |
| SEQ ID NO: 15 | TF-mAb-H34 | TF-mAb-H35 | TF-mAb-H36 | TF-mAb-H37 | TF-mAb-H38 |
| SEQ ID NO: 16 | TF-mAb-H39 | TF-mAb-H40 | TF-mAb-H41 | TF-mAb-H42 | TF-mAb-H43 |
| SEQ ID NO: 17 | TF-mAb-H44 | TF-mAb-H45 | TF-mAb-H46 | TF-mAb-H47 | TF-mAb-H48 |

Firstly, the 20 humanized antibodies were tested for their affinity for the extracellular domain protein of TF by ELISA binding assay (as to the experimental method, please refer to Step ④ of Example 1). The result was shown in Table 1.

TABLE 1

The binding affinity of humanized antibodies for the extracellular domain protein of TF

| Antibody | EC$_{50}$ (nM) | Antibody | EC$_{50}$ (nM) |
|---|---|---|---|
| TF-mAb-Ch | 0.0100 | TF-mAb-H39 | 0.0125 |
| TF-mAb-H29 | 0.0178 | TF-mAb-H40 | 0.0131 |
| TF-mAb-H30 | 0.0147 | TF-mAb-H41 | 0.0134 |
| TF-mAb-H31 | 0.0145 | TF-mAb-H42 | 0.0128 |
| TF-mAb-H32 | 0.0168 | TF-mAb-H43 | 0.0116 |
| TF-mAb-H33 | 0.0189 | TF-mAb-H44 | 0.0120 |
| TF-mAb-H34 | 0.0154 | TF-mAb-H45 | 0.0138 |
| TF-mAb-H35 | 0.0105 | TF-mAb-H46 | 0.0119 |
| TF-mAb-H36 | 0.0234 | TF-mAb-H47 | 0.0130 |
| TF-mAb-H37 | 0.0173 | TF-mAb-H48 | 0.0153 |
| TF-mAb-H38 | 0.0178 | IgG (negative control) | >6.67 |

The 20 humanized antibodies at 10 μg/mL and 1 μg/mL were tested for their binding affinity for 1×10$^5$ MDA-MB-231 cells by flow cytometry, respectively. The result was shown in Table 2.

TABLE 2

The binding affinity of humanized antibodies for MDA-MB-231;

| | MFI | |
|---|---|---|
| Antibody | 10 μg/mL | 1 μg/mL |
| TF-mAb-Ch | 3544 | 3369 |
| TF-mAb-H29 | 3584 | 2958 |
| TF-mAb-H30 | 3240 | 2930 |
| TF-mAb-H31 | 3468 | 3079 |
| TF-mAb-H32 | 3009 | 2400 |
| TF-mAb-H33 | 2837 | 2420 |
| TF-mAb-H34 | 3272 | 2462 |
| TF-mAb-H35 | 3015 | 2931 |
| TF-mAb-H36 | 3094 | 3037 |
| TF-mAb-H37 | 2989 | 2459 |
| TF-mAb-H38 | 3152 | 2871 |
| TF-mAb-H39 | 3383 | 3177 |
| TF-mAb-H40 | 3311 | 3182 |
| TF-mAb-H41 | 3613 | 3004 |
| TF-mAb-H42 | 3350 | 2968 |
| TF-mAb-H43 | 3302 | 2818 |
| TF-mAb-H44 | 3428 | 3195 |
| TF-mAb-H45 | 3478 | 3101 |
| TF-mAb-H46 | 3410 | 3115 |
| TF-mAb-H47 | 3151 | 2995 |
| TF-mAb-H48 | 2903 | 2611 |
| IgG (negative control) | 0 | 0 |

Example 4 Preparation of an Antibody-Drug Conjugate, TF-mAb-MMAE

To a stock solution of TF-mAb-SC1, PBS/D (pH=7.4) buffer was added until its concentration reached 20 mg/ml, and then TF-mAb-SC1 was reduced with TCEP (2.6 eq) at 25° C. for 2 h. The resultant mixture was cooled on ice, and MMAE (6 eq) was directly added without purification. After reaction at 0° C. for 1 h, Cyst was added to stop the reaction. The excessive small molecules were removed by G25 desalting column, and the resultant fraction was placed in 10 mM PBS solution (pH 7.4), and stored at −80° C. for further use. The antibody-drug conjugate obtained was designated as TF-mAb-MMAE.

Example 5 Preparation of an Antibody-Drug Conjugate, TF-mAb-DM1

① One-Step Preparation

Firstly, a stock solution of TF-mAb-SC1 was replaced by a G25 desalting column into a reaction buffer (50 mM potassium phosphate/50 mM NaCl/2 mM EDTA, pH 7.5) to a final concentration of 7.8 mg/ml; and then 9 eq of 11 mg/ml MCC-DM1 (dissolved in DMA, wherein the DMA content in the reaction system was less than 5%) was added. The reaction was carried out at room temperature for 6 h.

After centrifugation, the supernatant was purified by Q column and cation column purification to remove the excessive small molecules, and finally was replaced into 10 mM PBS solution by G25 desalting column or ultrafiltration, and stored at −80° C. for further use. The antibody-drug conjugate obtained was designated as TF-mAb-DM1.

② Two-Step Preparation

A stock solution of TF-mAb-SC1 was replaced by a G25 desalting column into a reaction buffer (50 mM potassium phosphate/50 mM NaCl/2 mM EDTA, pH 6.5) to a final concentration of 10 mg/ml; and then 8 eq of SMCC (dissolved in DMSO) was added. The reaction was carried out at 10-12° C. for 3 h, and the excessive SMCC was removed by G25 desalting column. DM1 (12 eq) was added to P-MCC, and the reaction was carried out at 25° C. for 18 h, and finally was replaced into 10 mM PBS solution by G25 desalting column, and stored at −80° C. The antibody-drug conjugate obtained was designated as TF-mAb-DM1.

Example 6 In Vitro Antitumor Activity of TF-mAb-ADCs Against Triple-Negative Breast Cancer Cells and Pancreatic Cancer Cells with High TF Expression The cell lines used in this Example were purchased from the American Type Culture Collection (ATCC) or the Cell Bank of Chinese Academy of Sciences, and cultured according to the corresponding instructions, including: MCF7, MDA-453, T47D, A549, U87MG, H1975, MDA-MB-231, BxPC-3, HCC1806, and Hs578T.

The cells in logarithmic growth phase were seeded into a 96-well culture plate at a density of 1,000-3,000 cells per well (depending on the growth rate of different cells) at 150 µL/well. After incubation at 37° C., 5% $CO_2$ for about 16 h, TF-mAb-ADCs (i.e. TF-mAb-DM1 and TF-mAb-MMAE) at different concentrations were added, each drug concentration was repeated in three wells, and the corresponding medium control and blank control wells were used. After incubation for 4 d, the culture solution was discarded, and MTS reaction solution (purchased from Promega, cat #G3581) was added at 100 µL/well. The reaction was carried out at 37° C. until the desired color depth was obtained, the cell viability (OD490 nm) of each group was determined, and cell viability was calculated according to the following formula:

Cell viability=$(OD_{administration}-OD_{blank})/(OD_{control}-OD_{blank})\times 100\%$.

The data above was analyzed by GraphPad Prism 5 software, and the $IC_{50}$ values of TF-mAb-DM1 and TF-mAb-MMAE for different cell lines were calculated, respectively.

Figure 2:
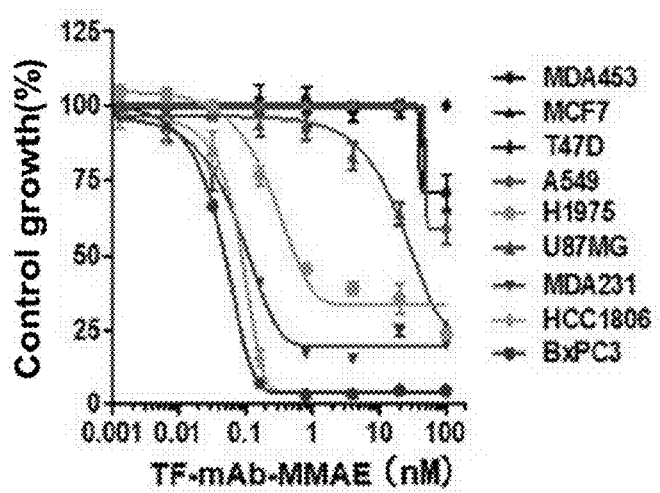
FIG. 2 shows that TF-mAb-MMAE could significantly inhibit the growth of tumor cells with high TF expression and the inhibition is proportional to TF molecules on the cell surface, wherein the left figure was the curve showing that TF-mAb-MMAE could well inhibit the growth of tumor cells with high TF expression, and the right table showed the $IC_{50}$ values of TF-mAb-MMAE for different cell lines.

The experimental results showed that both TF-mAb-DM1 and TF-mAb-MMAE could well inhibit the growth of tumor cells with high TF expression in vitro, and the inhibitory effect was proportional to the number of TF molecules on the cell surface. As shown in FIG. 1, the left figure was the curve showing that TF-mAb-DM1 could well inhibit the growth of tumor cells with high TF expression, and the right table showed the $IC_{50}$ values of TF-mAb-DM1 for different cell lines. As shown in FIG. 2, the left figure was the curve showing that TF-mAb-MMAE could well inhibit the growth of tumor cells with high TF expression, and the right table showed the $IC_{50}$ values of TF-mAb-MMAE for different cell lines.

Figure 3A:
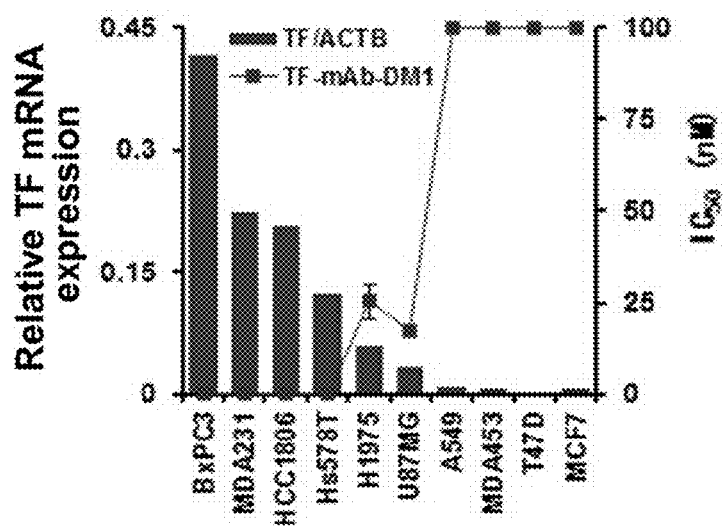
FIGS. 3A and 3B show the inhibitory effect of TF-mAb-DM1 (FIG. 3A) and TF-mAb-MMAE (FIG. 3B) on the growth of different tumor cells which was proportional to the TF molecules on the cell surface. By analyzing the relative TF molecule number on cell surface of different tumor cells using CCLE database (Arrays_2013 Mar. 18.tar.gz, Broad-Novartis Cancer Cell line Encyclopedia), the result shows that the inhibitory effect of TF-mAb-DM1 on the growth of different cells was proportional to the molecule number of TF on cell surface.
Figure 3B:
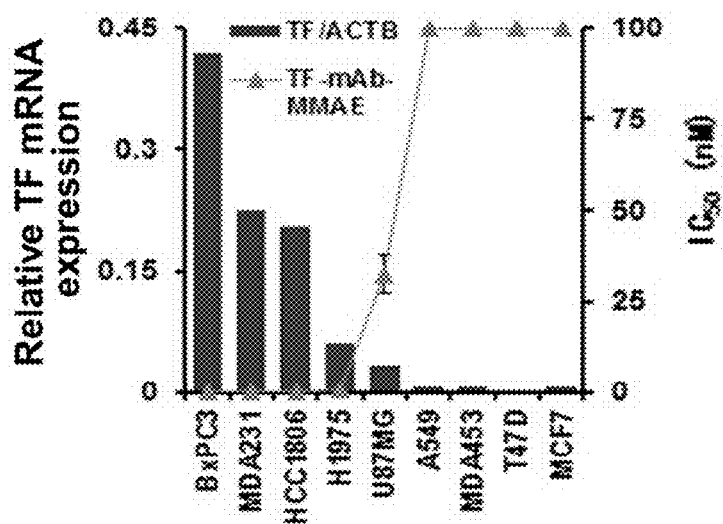

The relative molecule number of TF on different cell surfaces was analyzed by CCLE database (Broad-Novartis Cancer Cell line Encyclopedia), and the results showed that the inhibitory effect of TF-mAb-DM1 and TF-mAb-MMAE on the growth of different cells was proportional to the molecule number of TF on the cell surface, which were shown in FIG. 3A and FIG. 3B, respectively.

Example 7 In Vivo Antitumor Activity of TF-mAb-ADCs Against Triple-Negative Breast Cancer and Pancreatic Cancer Models with High TF Expression HCC1806 and BxPC-3 cells in logarithmic growth phase were used to inoculate 6-week old Balb/c female nude mice at the back subcutaneously or at mammary fatty pad at a density of $3\times10^6$ and $10\times10^6$ per 200 µL serum-free medium, respectively (Balb/c nude mice were purchased from Shanghai Xipuer-Beikai Experimental Animal Co., Ltd.). After the tumors grew to 100-200 $mm^3$, the animals were randomly grouped, with 8 tumors for each group. The mice were administered with TF-mAb-DM1 at a dose of 3.75 mg/kg and 15 mg/kg, or administered with TF-mAb-MMAE at a dose of 0.7 mg/kg, 2 mg/kg, 3.75 mg/kg, 7 mg/kg and 15 mg/kg once a week via tail vein. Normal mouse IgG (IgG) and docetaxel were used as negative and positive control drugs, respectively. The tumor volume and the weight of nude mice were measured 2-3 times a week and recorded so as to plot the tumor growth curve. Tumor volume (V) was calculated according to the following formula:

$V=\frac{1}{2}\times a\times b^2$, wherein a and b represented the length and width of tumor, respectively.

Figure 4A:
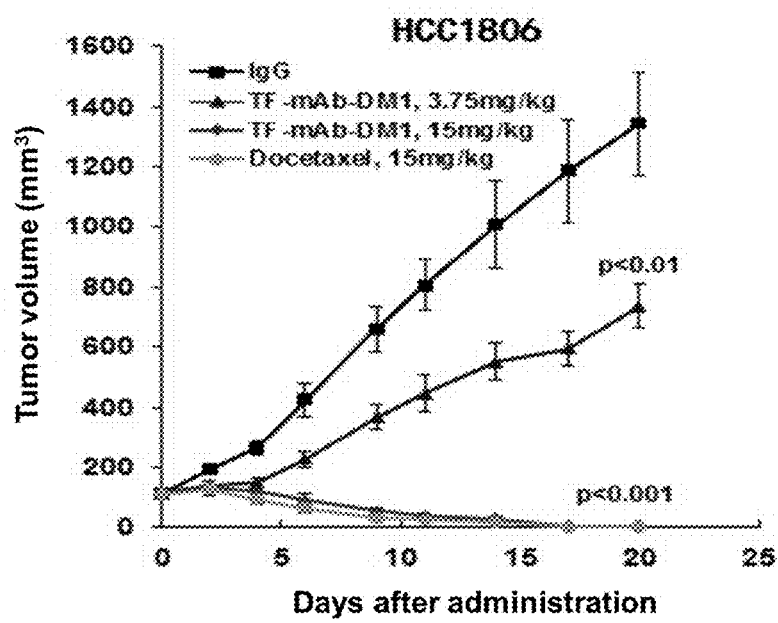
FIG. 4A shows that TF-mAb-DM1 could effectively inhibit the growth of HCC1806 xenograft tumor in a dose-dependent manner. Compared with the Docetaxel group, the mice in the TF-mAb-DM1 group hardly exhibited any weight loss, indicating that TF-mAb-DM1 had lower toxic side-effects.
Figure 4B:
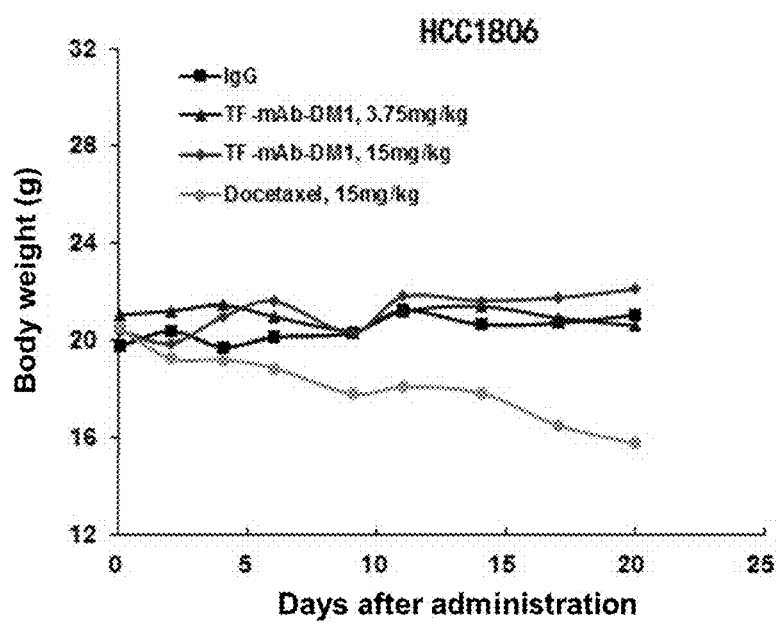
FIG. 4B shows the body weight curve of nude mice.

As shown in FIG. 4, FIG. 4A shows the curve that HCC1806 xenograft tumor growth was inhibited by TF-mAb-DM1 in a certain dose-dependent manner. FIG. 4B showed the curve on the change in body weight of nude mice.

Figure 5A:
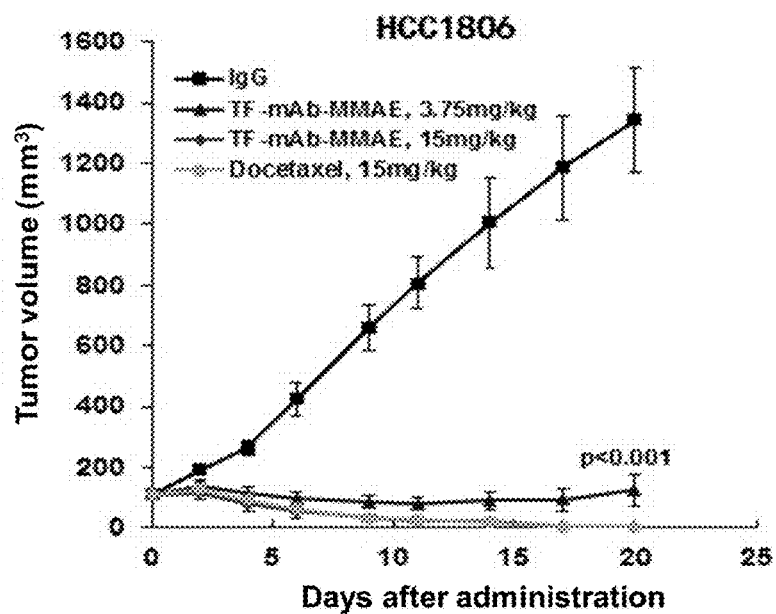
FIG. 5A shows that TF-mAb-MMAE could effectively inhibit the growth of HCC1806 xenograft tumor at different doses in a dose-dependent manner. Particularly, TF-mAb-MMAE, could almost completely inhibit the growth of HCC1806 orthotopically transplanted tumor at a dose of 3.75 mg/kg. Compared with the Docetaxel group, the mice in TF-mAb-MMAE group exhibited almost no weight loss, indicating that TF-mAb-MMAE had lower toxic side-effects.
Figure 5B:
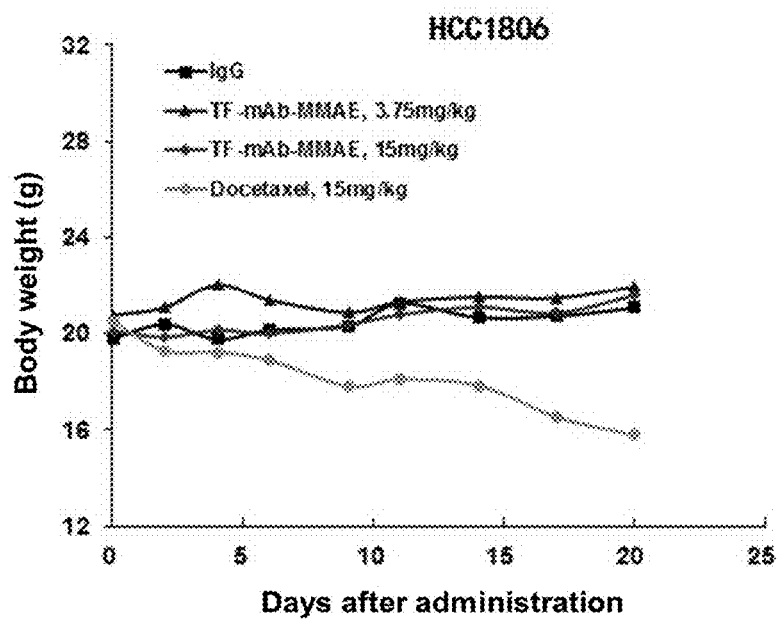
FIG. 5B shows the body weight curve of nude mice.
Figure 6:
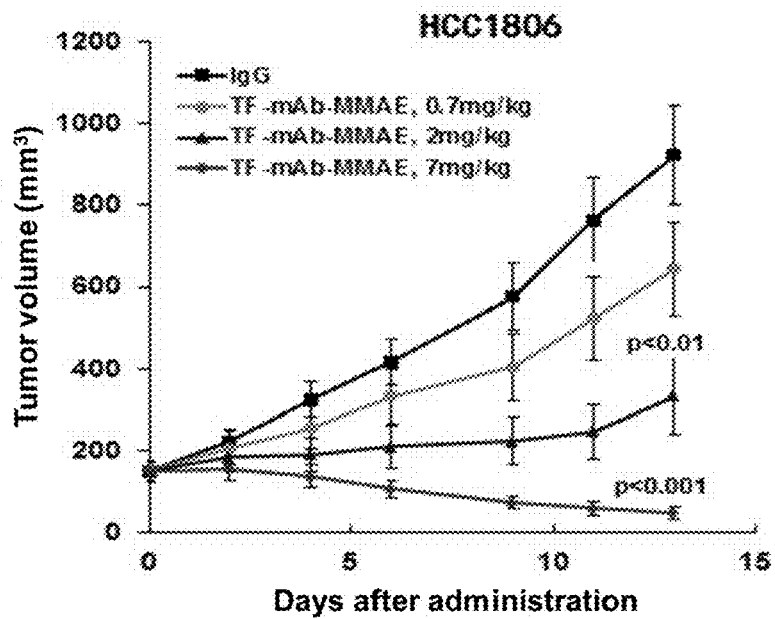
FIG. 6 shows that TF-mAb-MMAE could also inhibit the growth of HCC1806 xenograft tumor effectively at lower doses, and the experiment shows that the Minimum Effect Dose was 0.7 mg/kg.

FIG. 5A and FIG. 6 showed the curves that HCC1806 xenograft tumor growth was inhibited by TF-mAb-MMAE at different doses, and FIG. 5B showed the curve on the change in body weight of nude mice. It could be seen from the results that TF-mAb-MMAE could effectively inhibit the growth of HCC1806 tumor at a dose of 0.7 mg/kg, and could almost completely inhibit the growth of HCC1806 at a dose of 3.75 mg/kg.

Figure 7A:
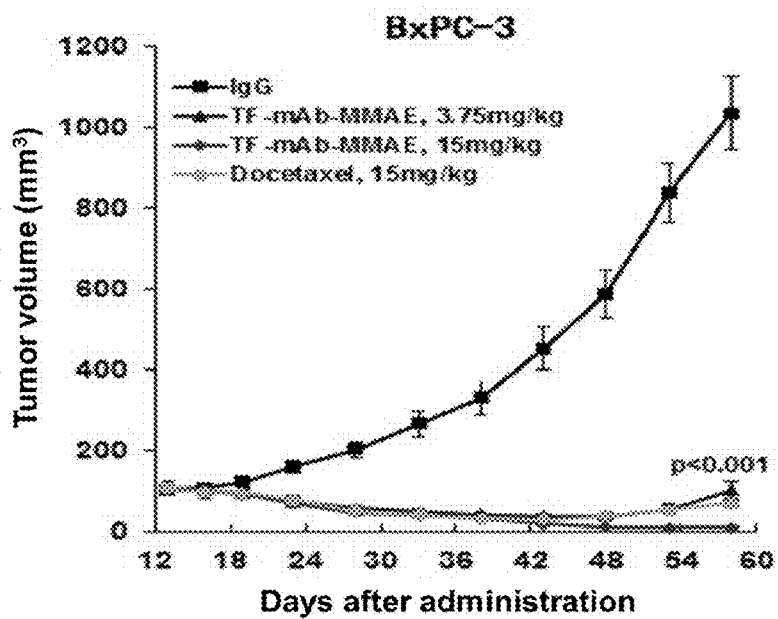
FIG. 7A shows that TF-mAb-MMAE could effectively inhibit the growth of BxPC-3 subcutaneously transplanted tumor in a dose-dependent manner. Compared with the Docetaxel group, the mice in TF-mAb-MMAE group exhibited almost no body weight loss, indicating that TF-mAb-MMAE had lower toxic side-effects.
Figure 7B:
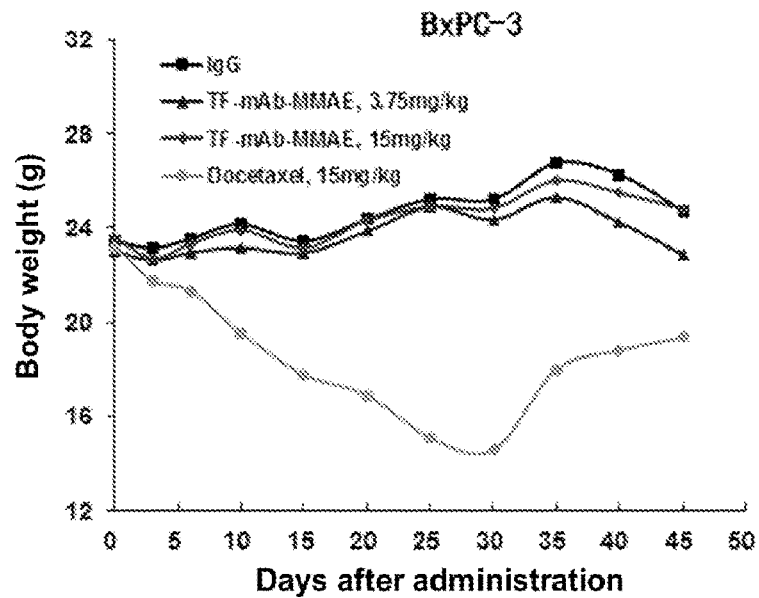
FIG. 7B shows the body weight curve of nude mice.

As shown in FIG. 7A, TF-mAb-MMAE could effectively inhibit the growth of BxPC-3 xenograft tumor in a dose-dependent manner. Compared with the mice in Docetaxel group, the mice in TF-mAb-MMAE group exhibited no body weight loss, indicating that TF-mAb-MMAE had lower toxic side-effects. FIG. 7B showed the curve on the change in body weight of nude mice.

Example 8 ADCs of Humanized Antibodies

Examples 4-7 were repeated, except that TF-mAb-SC1 was replaced by the following humanized antibody: TF-mAb-H29, TF-mAb-H30, TF-mAb-H31, TF-mAb-H32, TF-mAb-H33, TF-mAb-H34, TF-mAb-H35, TF-mAb-H36, TF-mAb-H37, TF-mAb-H38, TF-mAb-H39, TF-mAb-H40, TF-mAb-H41, TF-mAb-H42, TF-mAb-H43, TF-mAb-H44, TF-mAb-H45, TF-mAb-H46, TF-mAb-H47, and TF-mAb-H48.

Then, the conjugates of theses humanized antibodies with MMAE were prepared, respectively, wherein the characterization results of TF-mAb-H39-MMAE and TF-mAb-H44-MMAE were shown below.

Figure 8:
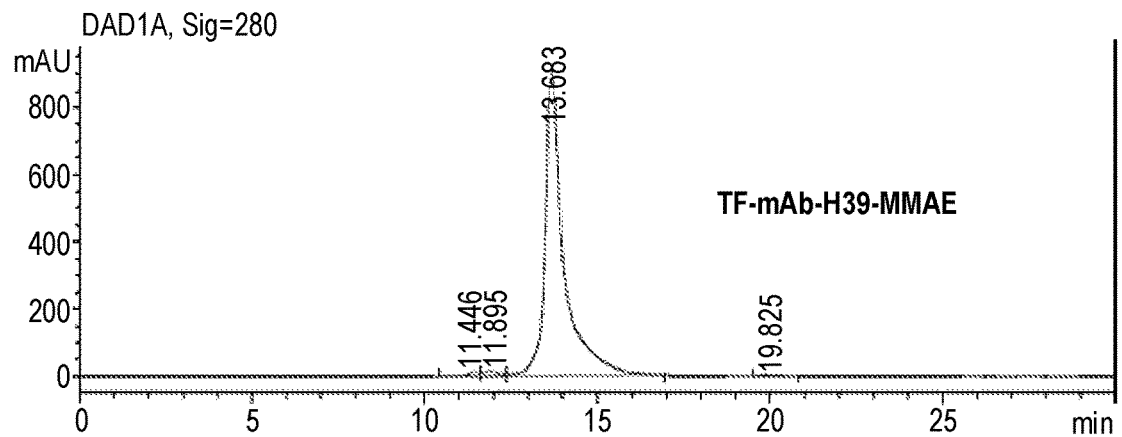
FIG. 8 shows the molecular sieve HPLC result of TF-mAb-H39-MMAE.
Figure 9:
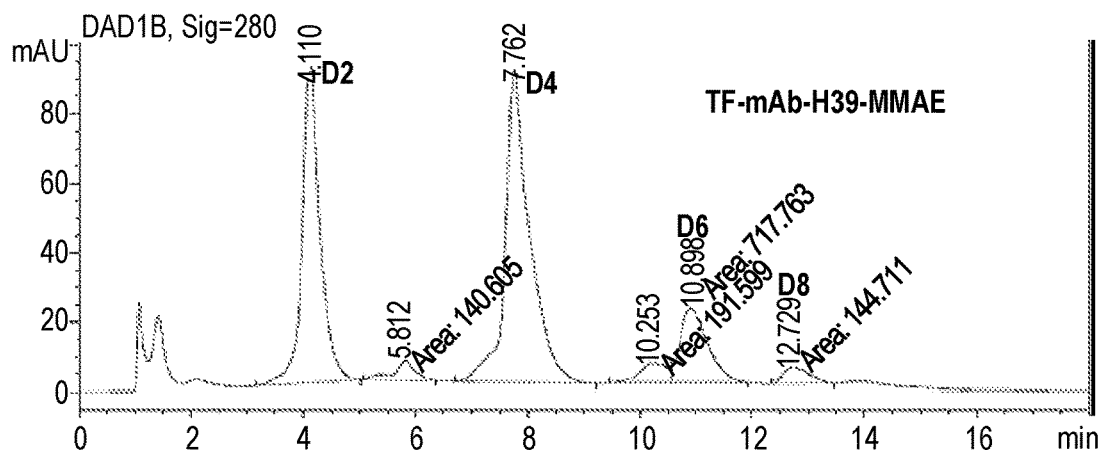
FIG. 9 shows the hydrophobic chromatographic result of TF-mAb-H39-MMAE.
Figure 10:
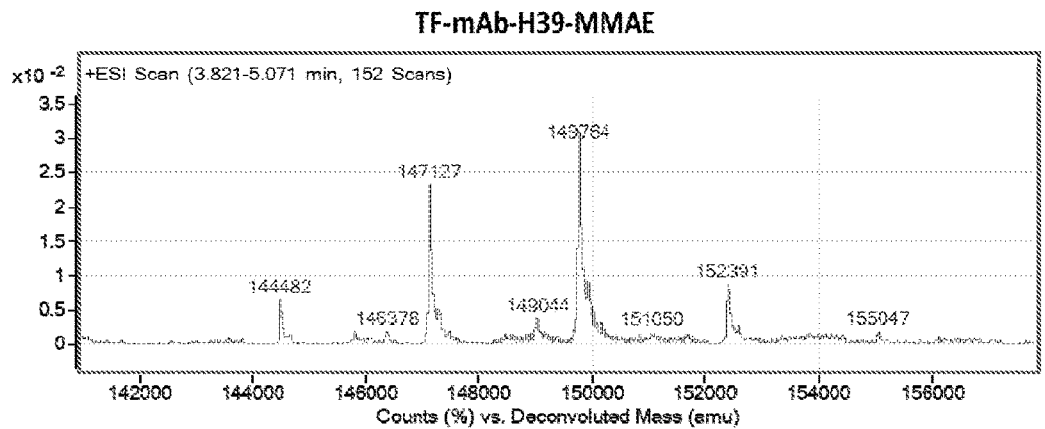
FIG. 10 shows the result of TF-mAb-H39-MMAE as characterized by mass spectrometry.
Figure 11:
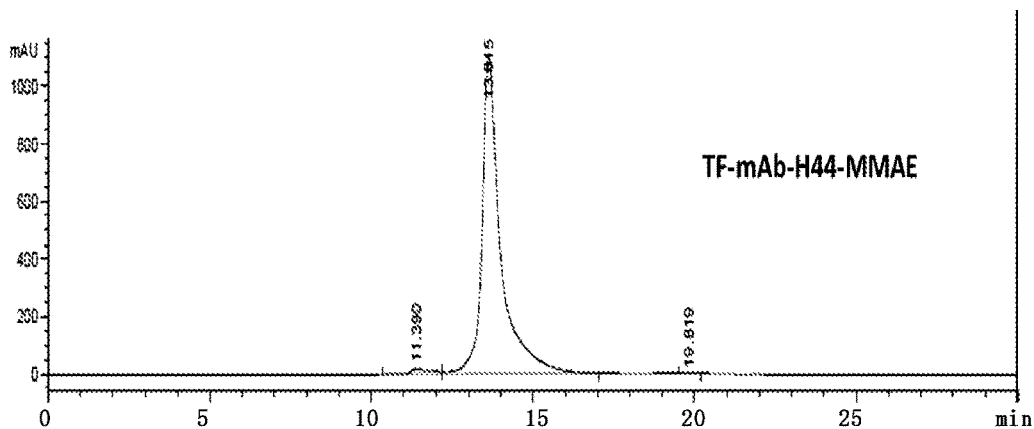
FIG. 11 shows the molecular sieve HPLC result of TF-mAb-H44-MMAE.
Figure 12:
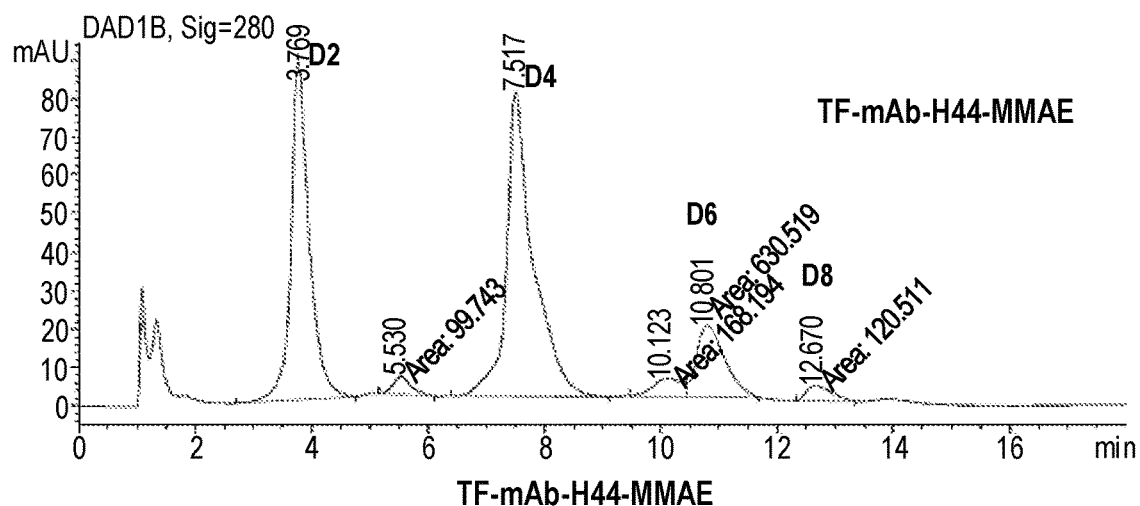
FIG. 12 shows the hydrophobic chromatographic result of TF-mAb-H44-MMAE.
Figure 13:
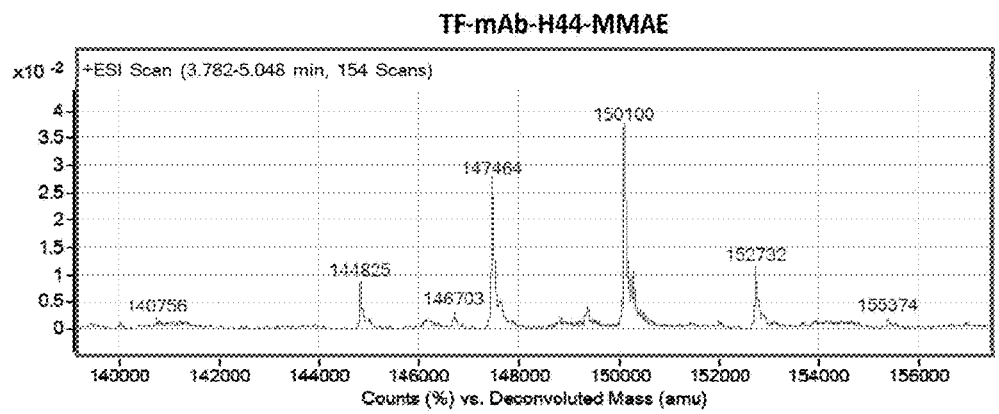
FIG. 13 shows the result of TF-mAb-H44-MMAE as characterized by mass spectrometry.

FIG. 8 showed the the molecular sieve HPLC of TF-mAb-H39-MMAE; FIG. 9 showed the hydrophobic chromatography of TF-mAb-H39-MMAE; FIG. 10 showed the mass spectrum of TF-mAb-H39-MMAE; FIG. 11 showed the the molecular sieve HPLC of TF-mAb-H44-MMAE; FIG. 12 showed the hydrophobic chromatography of TF-mAb-H44-MMAE; and FIG. 13 showed the mass spectrum of TF-mAb-H44-MMAE.

As calculated according to the experimental results above, TF-mAb-H39-MMAE and TF-mAb-H44-MMAE mainly had a drug-antibody ratio (DAR) of 2 and 4, and the average DAR was about 4.

The test results showed that the ADCs based on these humanized antibodies also have a high affinity (as compared with TF-mAb-MMAE, the ADC of a preferred humanized antibody had a relative affinity ranging between 60% and 140%), a high cytotoxicity, and lower toxic side-effects, and exhibited a significant anti-tumor effect.

The results on the in vitro and in vivo anti-tumor activity of two preferred humanized antibodies TF-mAb-H39-MMAE and TF-mAb-H44-MMAE were shown in FIG. 14 to FIG. 20, respectively.

Figure 14:
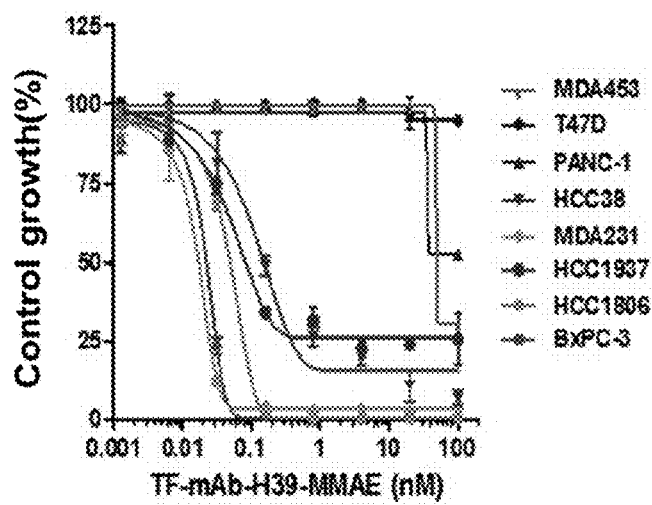
FIG. 14 shows that TF-mAb-H39-MMAE could significantly inhibit the growth of tumor cells with high TF expression, and was proportional to the molecule number of TF on the cell surface, wherein the table on the right panel shows the corresponding $IC_{50}$ values.

As shown in FIG. 14, the experimental result showed that TF-mAb-H39-MMAE could significantly inhibit the growth of tumor cells with high TF expression, and was proportional to the molecule number of TF on the cell surface, wherein the right table showed the $IC_{50}$ values of TF-mAb-H39-MMAE for different cell lines.

Figure 15:
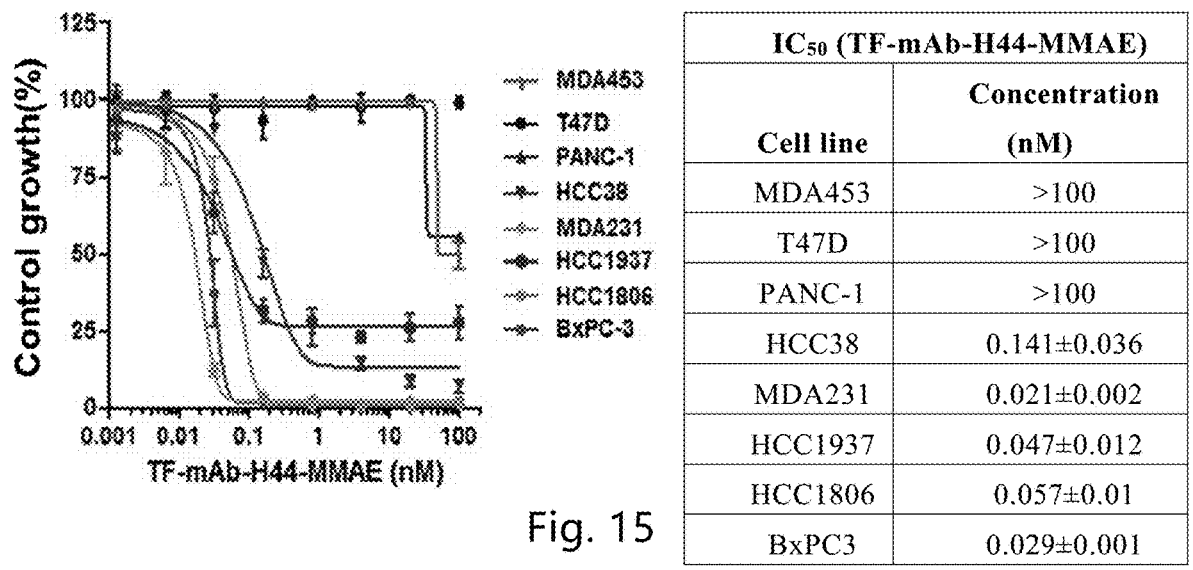
FIG. 15 shows that TF-mAb-H44-MMAE could significantly inhibit the growth of tumor cells with high TF expression, and the inhibitory effect was proportional to the molecule number of TF on the cell surface, wherein the table on the right panel shows the corresponding $IC_{50}$ values.

As shown in FIG. 15, TF-mAb-H44-MMAE could significantly inhibit the growth of tumor cells with high TF expression, and the inhibitory effect was proportional to the molecule number of TF on the cell surface, wherein the right table showed the $IC_{50}$ values of TF-mAb-H44-MMAE for different cell lines.

Figure 16A:
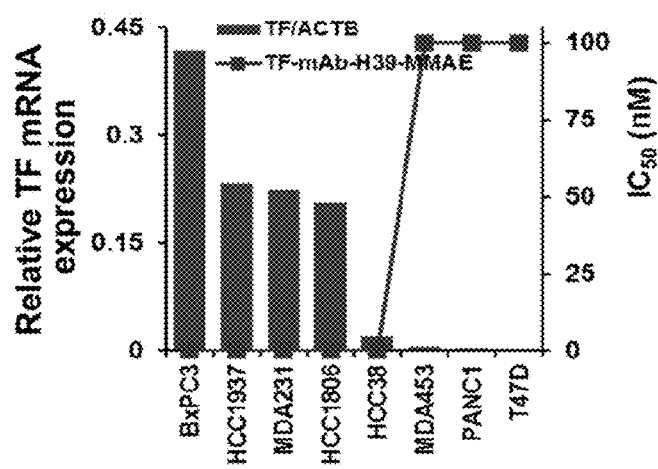
FIGS. 16A and 16B shows the analysis of the relative molecule number of TF on cell surface of different cells by CCLE database (Arrays_2013 Mar. 18.tar.gz, Broad-Novartis Cancer Cell line Encyclopedia), and the result shows that the killing effect of TTF-mAb-H39-MMAE (FIG. 16A) and TTF-mAb-H44-MMAE (FIG. 16B) on different cells was proportional to the molecule number of TF on cell surface.
Figure 16B:
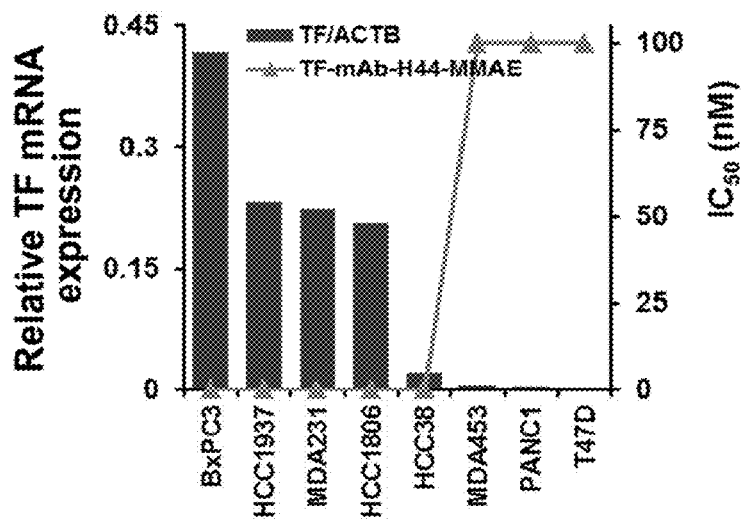

The relative molecule number of TF on different cell surfaces was analyzed by CCLE database, and the result showed that the killing effect of TF-mAb-H39-MMAE and TF-mAb-H44-MMAE on different cells was proportional to the molecule number of TF on the cell surface, which were shown in FIG. 16A and FIG. 16B, respectively.

Figure 17:
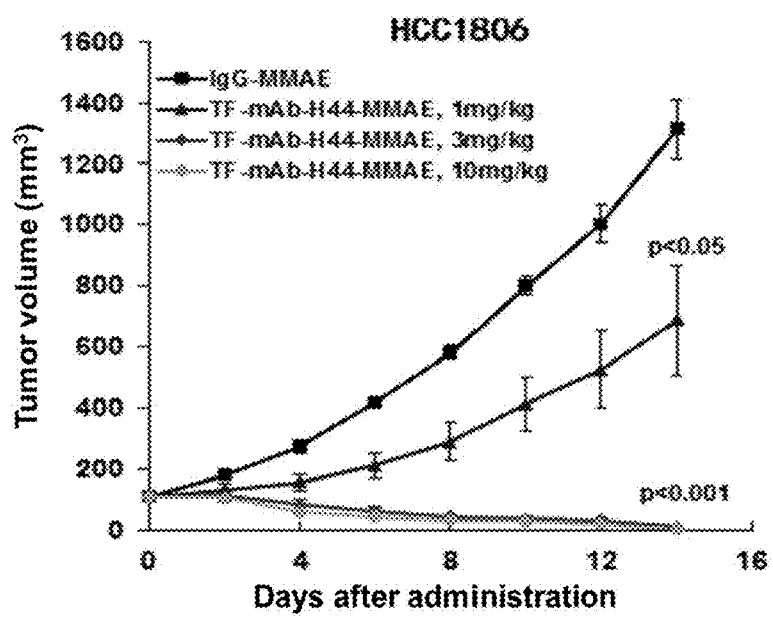
FIG. 17 shows that TF-mAb-H44-MMAE could effectively inhibit the growth of HCC1806 xenograft tumor, and could completely inhibit the growth of HCC1806 tumor at a dose of 3 mg/kg.

As shown in FIG. 17, TF-mAb-H44-MMAE could effectively inhibit the growth of HCC1806 xenograft tumor in a dose-dependent manner, and could completely inhibit HCC1806 tumor growth at a dose of 3 mg/kg, and the Minimum Effect Dose (MED) was 1 mg/kg.

Figure 18:
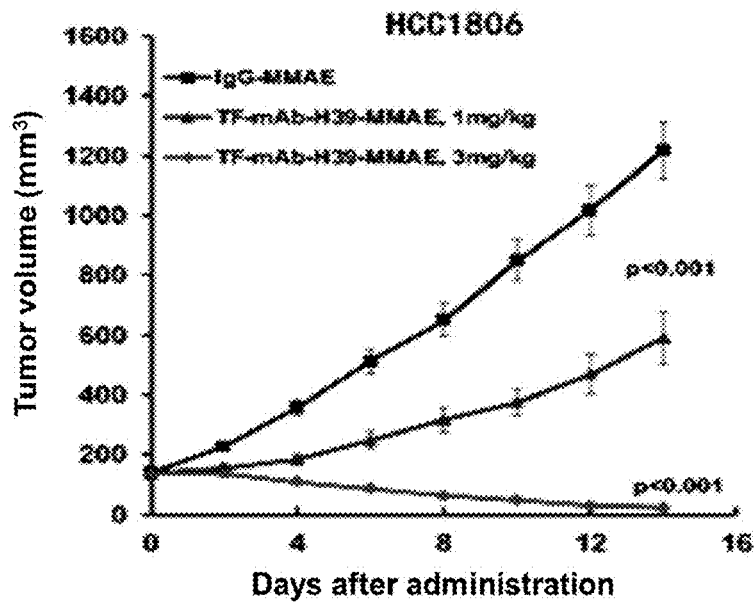
FIG. 18 shows that TF-mAb-H39-MMAE could effectively inhibit the growth of HCC1806 xenograft tumor, and its Minimum Effective Dose was 1 mg/kg.

As shown in FIG. 18, TF-mAb-H39-MMAE could effectively inhibit the growth of HCC1806 xenograft tumor, and the Minimum Effect Dose (MED) was 1 mg/kg.

Figure 19:
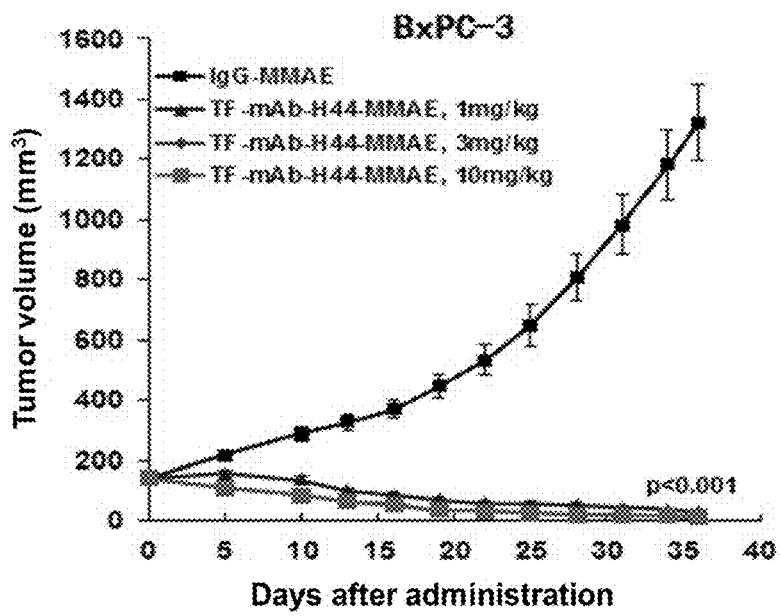
FIG. 19 shows that TF-mAb-H44-MMAE could effectively inhibit the growth of BxPC-3 xenograft tumor, and could completely inhibit the growth of BxPC-3 xenograft tumor at a dose of 1 mg/kg.

As shown in FIG. 19, TF-mAb-H44-MMAE could significantly inhibit the growth of BxPC-3 xenograft tumor in a dose-dependent manner, and could completely inhibit BxPC-3 tumor growth at a dose of 1 mg/kg.

Figure 20:
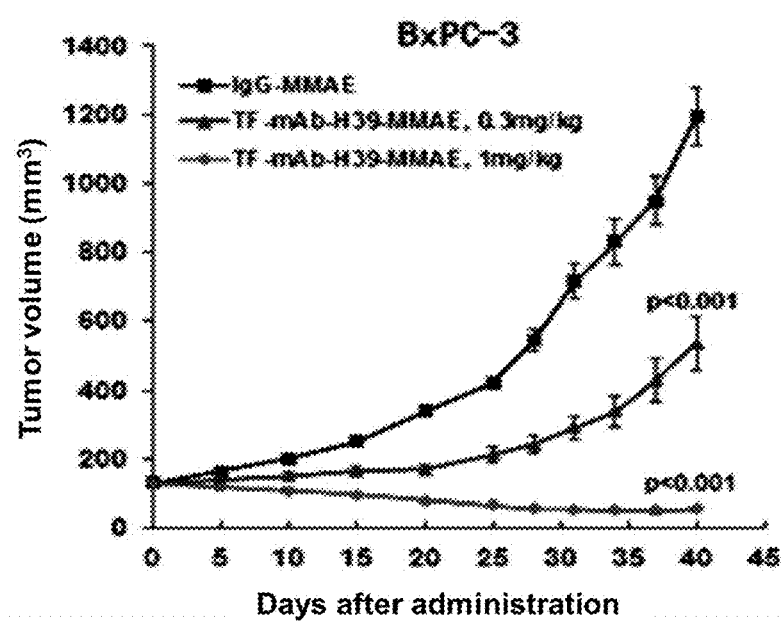
FIG. 20 shows that TF-mAb-H39-MMAE could effectively inhibit the growth of BxPC-3 xenograft tumor, and its Minimum Effective Dose was 0.3 mg/kg.

As shown in FIG. 20, TF-mAb-H39-MMAE could significantly inhibit the growth of BxPC-3 xenograft tumor, and the Minimum Effective Dose (MED) was 0.3 mg/kg.

All the documents mentioned in the present invention are incorporated in the present application by reference to the same extent as if each individual document is specifically and individually indicated to be incorporated by reference. In addition, it should be understood that after reading the contents taught in the present invention, various modifications and changes may be made to the present invention by those skilled in the art, and these equivalents also fall into the scope defined by the claims.

The invention claimed is:

1. A method for treating a tissue factor (TF)-related disease, comprising administering a therapeutically effective amount of the antibody-drug conjugate or a pharmaceutical composition comprising the antibody-drug conjugate to a subject in need thereof,
   wherein the antibody-drug conjugate comprises:
   (a) an antibody moiety, wherein the heavy chain variable region of the antibody comprises the following three complementary determining regions (CDRs):
   (H1) CDR1 as set forth in SEQ ID NO: 1,
   (H2) CDR2 as set forth in SEQ ID NO: 2, and
   (H3) CDR3 as set forth in SEQ ID NO: 3, and
      the light chain variable region of the antibody comprises the following three complementary determining regions (CDRs):
      (L1) CDR1' as set forth in SEQ ID NO: 4,
      (L2) CDR2' as set forth in SEQ ID NO: 5, and
      (L3) CDR3' as set forth in SEQ ID NO: 6, and
   (b) a conjugation moiety conjugated to the antibody moiety, wherein the conjugation moiety is Monomethyl auristatin E (MMAE); and
   wherein the TF-related disease is tumorigenesis, tumor growth, or tumor metastasis, the tumor is a tumor with high TF expression, and the tumor is pancreatic cancer, triple negative breast cancer, cervical cancer, lung cancer or malignant glioma.

2. The method according to claim 1, wherein the antibody-drug conjugate (ADC) has a formula as follows:

wherein:

Ab is an anti-TF antibody,

LU is a linker;

D is the conjugate moiety;

and the subscript p is a value selected from 1-10.

3. The method according to claim 1, wherein the antibody is an animal-derived antibody, a chimeric antibody, a humanized antibody, or a combination thereof.

4. The method according to claim 1, wherein the sequence of the heavy chain variable region of the antibody is selected from the group consisting of SEQ ID NOS: 7, 9, 10, 11, 12, and 13.

5. The method according to claim 1, wherein the sequence of the light chain variable region of the antibody is selected from the group consisting of SEQ IDS NO: 8, 14, 15, 16, and 17.

6. The method according to claim 4, wherein the sequence of the light chain variable region of the antibody is selected from the group consisting of SEQ IDS NO: 8, 14, 15, 16, and 17.

7. The method according to claim 1, wherein the antibody is selected from the group consisting of TF-mAb-SC1, TF-mAb-Ch, TF-mAb-H29, TF-mAb-H30, TF-mAb-H31, TF-mAb-H32, TF-mAb-H33, TF-mAb-H34, TF-mAb-H35, TF-mAb-H36, TF-mAb-H37, TF-mAb-H38, TF-mAb-H39, TF-mAb-H40, TF-mAb-H41, TF-mAb-H42, TF-mAb-H43, TF-mAb-H44, TF-mAb-H45, TF-mAb-H46, TF-mAb-H47, and TF-mAb-H48.

8. The method according to claim 1, wherein the antibody is TF-mAb-H39 or TF-mAb-H44.

9. The method according to claim 1, wherein the tumor is triple negative breast cancer.

10. The method according to claim 1, wherein the tumor is pancreatic cancer.

11. The method according to claim 1, wherein the tumor is cervical cancer.

12. The method according to claim 1, wherein the tumor is lung cancer.

13. The method according to claim 1, wherein the tumor is malignant glioma.

* * * * *